United States Patent [19]
Corthésy-Theulaz

[11] Patent Number: 6,060,241
[45] Date of Patent: May 9, 2000

[54] COMPOSITIONS AND METHODS RELATING TO DRUG DISCOVERY AND DETECTION AND TREATMENT OF GASTROINTESTINAL DISEASES

[75] Inventor: Irene Corthésy-Theulaz, Epalinges, Switzerland

[73] Assignee: Kieta Holding SA, St-Prex, Switzerland

[21] Appl. No.: 08/834,776

[22] Filed: Apr. 3, 1997

Related U.S. Application Data

[60] Provisional application No. 60/014,906, Apr. 5, 1996.

[51] Int. Cl.$^7$ ...................................................... C12Q 1/70
[52] U.S. Cl. .............................................. 435/6; 536/23.2
[58] Field of Search ................................ 536/23.2; 435/6

[56] References Cited

U.S. PATENT DOCUMENTS 5,512,669  4/1996  Peoples .................................. 536/23.2

FOREIGN PATENT DOCUMENTS 0 649 906    4/1995   European Pat. Off. .
9100917      1/1991   WIPO .
9302194      2/1993   WIPO .
95 33767    12/1995   WIPO .

OTHER PUBLICATIONS

Blaser M.J., "The Bacteria behind Ulcers," Scientific American, pp. 104–107, Feb. 1996.

Blaser M.J., "Parasitism by the "Slow" Bacterium *Helicobacter pylori* Leads to Altered Gastric Homeostatis and Neoplasis," The Journal of Clinical Investigation, Inc., vol. 94:4–8 (1994).

Cary et al., "Cloning and Expression of *Clostridium acetobutylicum* ATCC 824 Acetoacetyl–Coenzyme A:Acetate/Butyrate:Coenzyme A–Transferase in *Escherichia coli*," Applied and Environmental Microbiology, vol. 56(6):1576–1583 (1990).

Chalk et al., "Metabolism of pyruvate and glucose by intact cells of *Helicobactoer pylori* studies by $^{13}$C NMR spectroscopy," Microbiology, vol. 140:2085–2092 (1994).

Cover et al., "*Helicobacter pylori*: A Bacterial Cause of Gastritis, Peptic Ulcer Disease, and Gastric Cancer," ASM News, vol. 61(1):21–26 (1995).

Doten et al., "Cloning and Genetic Organization of the pca Gene Cluster from *Acinetobacter calcoaceticus*," Journal of Bacteriology, vol. 169(7): 3168–3174 (1987).

Hua et al., *Helicobacter pylori*: techniques for clinical diagnosis and basic research, Chap. 9:121–127, Edited by: A. Lee & F. Megraud, WB Saunders Company LTD (1996).

Lin et al., "Sequence of a cDNA Clone Encoding Pig Heart Mitochondrial CoA Transferase," The Journal of Biological Chemistry, vol. 267(2):975–978 (1992).

Mendes et al., Ultrastructure of a spiral micro–organism from pig gastric mucosa ("*Gastrospirillum suis*"), J. Med. Microbiol., vol. 33:61–66 (1990).

Mendz et al., "Pyruvate metabolism in *Helicobacter pylori*," Arch. Microbiol. vol. 162:187–192 (1994).

Mendz et al., "Aminoacid Utilization by *Helicobacter pylori*," Int. J. Biochem. Cell Biol., vol. 27(10):1085–1093 (1995).

Nedenskov et al., "Nutritional Requirements for Growth of *Helicobacter pylori*," Applied and Environmental Microbiology, vol. 60(9):3450–3453 (1994).

Parales et al., "Characterization of the Genes Encoding β–Ketoadipate: Succinyl–Coenzyme A Transferase in *Pseudomonas putida*," Journal of Bacteriology, vol. 174(14):4657–4666 (1992).

Reynolds et al., "Characteristics of *Helicobacter pylori* growth in a defined medium and determination of its amino acid requirements," Microbiology, vol. 140:2649–2656 (1994).

Segal et al., "*Helicobacter pylori* attachment to gastric cells induces cytoskeletal rearrangements and tyrosine phosphorylation of host cell proteins," Proc. Natl. Acad. Sci. USA, vol. 93:1259–1264 (1996).

Shanley et al., "Unusual G + C content and codon usage in catIJF, a segment of the bencat supra–operonic cluster in the *Acinetobacter calcoaceticus* chromosome," Gene, vol. 138:59–65 (1994).

Steinbuchel et al., "Physiology and molecular genetics of poly (β–hydroxy–alkanoic acid) synthesis in *Alcaligenes eutrophus*," Molecular Microbiology, vol. 5(3):535–542 (1991).

Tildon et al., "Succinyl–CoA: 3–Ketoacid CoA–Transferase Deficiency," The Journal of Clinical Investigation, vol. 51:493–498 (1972).

Walsh et al., "The Treatment of *Helicobacter Pylori* Infection in the Management of Peptic Ulcer Disease," The New England Journal of Medicine, vol. 333(15):984–991 (1995).

White et al., "Properties of Succcinyl–CoA:3–Ketoacid Coenzyme A Transferase," The Journal of Biological Chemistry, vol. 251(6):1708–1711 (1976).

(List continued on next page.)

*Primary Examiner*—James C. Housel
*Assistant Examiner*—Ginny Allen Portner
*Attorney, Agent, or Firm*—Cooley Godward LLP

[57] ABSTRACT

A poly-3-hydroxybutyrate metabolic pathway essential for *Helicobacter pylori* survival in a host is provided. A novel *Helicobacter pylori* Coenzyme A transferase (*Hp* CoA-t), thiolase and PHB synthase as well as methods for their preparation and use are provided. *Hp* CoA-t and thiolase polynucleotides and proteins are provided as well as detection and preparative methods using such molecules. Methods for the determination of a propensity to develop gastritis, peptic ulcer disease, or gastric cancer is provided for by detection methods. Methods are also provided for the use of *Hp* CoA-t, thiolase or PHB synthase proteins and fragments retaining enzymatic activity in the identification of potential drug candidates for the treatment of some types of gastric disease. Pharmaceutical compositions containing *Hp* CoA-t protein fragments, antisense nucleic acids or other inhibitors of *Hp* CoA-t, thiolase and PHB synthase as well as methods for their use in the treatment of some types of gastric disease are also provided.

12 Claims, 10 Drawing Sheets

OTHER PUBLICATIONS

Wiesenborn et al., "Coenzyme A Transferase from *Clostridium acetobutylicum* ATCC 824 and Its Role in the Uptake of Acids," Applied and Environmental Microbiology, vol. 55(2):323–329 (1989).

Bergonzelli G. et al., "The quest for new lethal targets of *Helicobacter pylori*: Cloning and expression of the 3–oxoacid–CoA transferase genes in *Escherichia coli*," Supplement to Gastroenterology, vol. 110(4):A863 (1996).

Petersen D. et al., "Sequence and arrangement of genes encoding enymes of the acetone–production pathway of *Clostridium acetobutylicum* ATCC 824," Gene, vol. 123(1):93–97 (1993).

Petersen, D.J. et al, Gene, vol. 123, 1993, pp. 93–97.

Dolby, J.M. et al, Scand. J. Gastroenterol, vol. 19, pp. 105–110, 1984.

Fleischman, R.D. et al, Science, vol. 269, pp. 469–512, 1995.

Christensen, JJ. et., Scand. J. Infect. Dis., 1990, vol. 22(4), 437–444, abs.

Blakey, JL et al, J. Med. Microbiol, vol. 15(4), pp. 519–530, abs. 1982.

Kraeft, H et al, Infection, Sep.–Oct. 1985, 13(5), pp. 211–215, (abs).

Pingleton et al, May 1986, Am. J. Med., vol. 60, pp. 827–831.

Sjostedt, S et al, Eur. J. Clin. Microbiol, Feb., vol. 4(1), 49–51, abs. 1985.

Sjostedt, S et al., Ann. Surg., Mar., vol. 207(3), pp. 341–346, 1988.

Petersen, D.J. et al, Gene, 1995, vol. 154, pp. 81–85.

Stim–Hendersen, K.P. et al, Appl. Environment. Microbiol, vol. 57, 2735–2741, 1991.

Petersen, D. et al (1993) Gene, vol. 123(1), pp. 93–97.

Bergonzelli et al (Apr. 1996) Supplement to Gastroenterolgy, vol. 110(4), pA 863.

Lin, T et al, J. Bact. Chem. 1992, vol. 267(2), Jan. 15, pp. 975–978.

Shanley et al, Gene, 1994, vol. 138, pp. 59–65.

Hoffman, P.S. et al, 1996, J. of Bacteriol., vol. 178, pp. 4822–4829 (abstract).

Kowalchuk, G.A et al, 1994, Gene, vol. 146, pp. 23–30 EMBL # L05770 and G141776.

Yoshida, K.I et al, 1995, Feb., EMBL # D83026 and D1012372.

Schembri, M.A et al, 1995, J. Bacteriol, vol. 177, p. 4501–4507 EMBL # L37761 and G576786.

Fleishmann, R.D. et al, 1995, Science, vol. 269, pp. 496–512 EMBL # U32761 and G1573781.

Tomb, J et al, 1997, Nature, vol. 388, Aug., pp. 539–547.

Parales, R.E. et al, Jul. 1992, J. Bacteriology, vol. 174(14) pp. 4657–4666.

Cary, J.W. et al, App. Environ. Microbiol., vol. 56(6), Jun. 1990, pp. 1576–1583.

Hughes, N.J. et al, J. Bacteriol., vol. 177(14), Jul. 1995, pp. 3953–3959.

FIG. 1A

```
     CGGGGCGGTCGTTGTGCCGTGGGCGGTCAAGGGCGTCTATCAGTGGTAGTTGAACAAAAATAAGAGAATGAGATGAACAAGGTTATAACC
  1  ---------+---------+---------+---------+---------+---------+---------+---------+ 90
                                                                      M  N  K  V  I  T

GATTTAGACAAAGCATTGAGCACATTAAAGAGACGGGGACACTATTTAGTGGGCGGTTTTGGGCTGTGCGGGATACCGCCATT
 91  ---------+---------+---------+---------+---------+---------+---------+---------+ 180
      D  L  D  K  A  L  S  T  L  K  D  G  D  T  I  L  V  G  G  F  G  L  C  G  I  P  E  Y  A  I

GATTACATTTATAAGAAAGGCATTAAGGATTTGATTGTCGTGAGCAATAATTGTGGCGTTGATGATTTTGGCTTGGCATTCTTTTAGAA
181  ---------+---------+---------+---------+---------+---------+---------+---------+ 270
      D  Y  I  Y  K  K  G  I  K  D  L  I  V  V  S  N  N  C  G  V  D  D  F  G  L  G  I  L  L  E

AAAAAGCAGATCAAAAAGATTATCGCTTCGTATGTGGGAGAAAATAAGATTTTTGAATCGCAAATGCTGAACGGAGAAATTGAAGTCGTT
271  ---------+---------+---------+---------+---------+---------+---------+---------+ 360
      K  K  Q  I  K  K  I  I  A  S  Y  V  G  E  N  K  I  F  E  S  Q  M  L  N  G  E  I  E  V  V

TTGACACCGCAAGGCACCCTGGCTGAAAACTTGCGCCCTGGAGGGCGTGGATACCGCTTACTACACCCAACCAGGGGTTGGACTTTA
361  ---------+---------+---------+---------+---------+---------+---------+---------+ 450
      L  T  P  Q  G  T  L  A  E  N  L  R  P  G  G  A  G  I  P  L  T  T  P  Q  P  G  V  G  T  L

ATCGCTCCAAGGCAAGGAATCCAAGGAGTTTAACGGCAAGGAGTATATTTTAGAAAGAGCCATAACAGGCGATTATGGCTTATCAAA
451  ---------+---------+---------+---------+---------+---------+---------+---------+ 540
      I  A  P  R  Q  G  I  Q  G  S  L  T  A  R  E  Y  I  L  E  R  A  I  T  G  D  Y  G  L  I  K

GCTTATAAAAGCAGACACTCTTGGGAATTTGTGTGTTTAGAAAAACAGCTAGAAATTTCAATCCCCTTGTGCGCAATGGCAGCAAAATATGC
541  ---------+---------+---------+---------+---------+---------+---------+---------+ 630
      A  Y  K  S  D  T  L  G  N  L  V  F  R  K  T  A  R  N  F  N  P  L  C  A  M  A  A  K  I  C

GTTGCTGAAGTGGAAGAAATTGTCCCGGCCGGGGAATTAGACCCAGATGAAATACACTTGCCAGGAATCTATGTGCAACATCTATAAG
631  ---------+---------+---------+---------+---------+---------+---------+---------+ 720
      V  A  E  V  E  E  I  V  P  A  G  E  L  D  P  D  E  I  H  L  P  G  I  Y  V  Q  H  I  Y  K
```

FIG. 1B

```
       GGGGAGAAATTTGAAAAACGGATAGAAAAATCACGACAAGGAGCGGCGAAAGAGAGCTATCATTAAAGAGCGGCAAAGGAACTAA
721    ---------+---------+---------+---------+---------+---------+---------+---------+     810
        G  E  K  F  E  K  R  I  E  K  I  T  T  R  S  A  K  *
                                                              M  R  E  A  I  I  K  R  A  A  K  E  L  K

AAGAGGGCATGTATGTGAATTTAGGAGATAGCCTTGCCCACGCTGTGGCCTAATGAAGTGAGCGGGATGAATATCGTTTTCCAGAGCGAGA
811    ---------+---------+---------+---------+---------+---------+---------+---------+     900
        E  G  M  Y  V  N  L  G  I  G  L  P  T  L  V  A  N  E  V  S  G  M  N  I  V  F  Q  S  E  N

ACGGGTTATTAGGGATTGGCGCTTACCCTTTAGAGGGGAGCGTTGATGCGGATCTCATCAACGCAGGAAAGGAAACCGTAACCGTGGTGC
901    ---------+---------+---------+---------+---------+---------+---------+---------+     990
        G  L  L  G  I  G  A  Y  P  L  E  G  S  V  D  A  D  L  I  N  A  G  K  E  T  V  T  V  V  P

CGGGGCGCTTCGTTTTCAATAGCGCGGATTCGTTTGCGATGATTCGTGGGGGCATATTGATTTAGGAGGATGAAGTCT
991    ---------+---------+---------+---------+---------+---------+---------+---------+     1080
        G  A  S  F  F  N  S  A  D  S  F  A  M  I  R  G  G  H  I  D  L  A  I  L  G  G  M  E  V  S

CACAAAAATGGGATTGGCTAATTGAATGGGAGCATGGAGGGCTATGATCGTGTGCATGGCGCTAAAA
1081   ---------+---------+---------+---------+---------+---------+---------+---------+     1170
        G  A  S  F  F  N  S  A  D  S  F  A  M  I  R  G  G  H  I  D  L  A  I  L  G  G  M  E  V  S
```
(Figure continues — DNA sequence with translated amino acid sequence below each codon, numbered 721 through 1395)

FIG. 2A

```
                                                                                     70
E.coli                                                      MK TKLMTLQDAT GFFRDQATIM VGGFMGIGTP
C.acet A                                                    MN SKIIRFENLR SFFKDGWTIM IGGFLNCGTP
A.calc A                                                   MID KSAATLTEAL SQIHDGATIL IGGFGTAGQP
P.puti A                                                   LIN KTYESIASAV EGITDGSTIM VGGFGTAGMP
H.pyl A                                        LNKNKENEMN KVITDLDKAL STLKDGDTIL VGGFGLCGIP
B.subt                                                      MG KVLSSSKEAA KLIHDGDTLI AGGFGLCGIP
Pig        MAALTLLSSR LRLCASAYRS GGAWSQGCAG YFSTSTRRHT KFYTDAVEAV KDIPNGATVL VGGFGLCGIP 71                                                                        140
E.coli     SRLVEALLES GVRDLTLIAN DTAFVDTGIG PLIVNGRVRK VIASHI..GT NPETGRKMIS GEMDVVLVPQ
C.acet A   TKLIDFLVNL NIKNLTIISN DTCYPNTGIG KLISNNQVKK LIASYI..GS NPDTGKKLFN NELEVELSPQ
A.calc A   AELIDGLIEL GRKNLTIVSN NAGNGDYGLA KLLKTGAVKK IICSFPRQAD SYVFDELYRA GKIELEIVPQ
P.puti A   SELIDGLIAT GARDLTIISN NAGNGEIGLA VVCSFPRQSD SYVFDELYFA GKIELEVVPQ
E.coli                                                                              
C.acet A                                                                            
A.calc A                                                                            
P.puti A                                                                            
H.pyl A    EYAIDYIYKK GIKDLIVSN NCGVDDFGLG ILLEKKQIKK IIASYV..GE NKIFESQMLN GEIEVLTPQ
B.subt     EQLILSIRDQ GVKDLTVSN NCGVDDWGLG LLLANKQIKK MIASYV..GE NKIFERQFLS GELEVELVPQ
Pig        ENLIGALLKT GVKELTAVSN NAGVDNFGLG LLLQSKQIKR MISSYV..GE NAEFERQYLA GELEVELTPQ 141                                                                       210
E.coli     GTLIEQIRCG GAGLGGFLTP TGVGTVVEEG ...........KQ TLTLDGKTWL LERPLRADLA
C.acet A   GTLVERIRAG GSGLGGVLTK TGLGTLIEKG ...........KK KISINGTEYL LELPLTADVA
A.calc A   GNLACRIQAA GMGLGPIYTP TGFGTLLAEG ...........KP TLNFDGKDYV LENPIKADFA
P.puti A   GNLAERIAAA GSGIGAFFSP TGYGTLLAEG ...........KE TREIDGRMYV LEMPLHADFA
H.pyl A    GTLAENLRPG GAGIPLTTPQ PGVGTL.... ........IAPRQGI QGSLTAREYI LERAITGDYG
B.subt     GTLAERIRAG GAGIPGFYTA TGVGTS.... .........IAEGKE. HKTFGGRTVV LERGITGDVA
Pig        GTLAERIRAG GAGVPAFYTS TGYGTLVQEG GSPIKYNKDG SIAIASKPRE VREFNGQHFI LEEAIRGDFA
```

FIG. 2B

```
           211                                                                          280
E.coli     LIRAHRCDTL GNLTYQLSAR NFNPLIALAA DITLVEPDEL VETGELQPDH IVPPGAVIDH IIVSQESK*
C.acet A   LIKGSIVDEA GNTFYKGTTK NFNPYMAMAA KTVIVEAENL VSCEKLEKEK AMTPGVLINY IVKEPA*
A.calc A   LIKAYKGDRW GNLVYRKSAR NFGPIMAMAA NVTLAQVSEV VALGELDPEN VVTPGIFVQH VVPVQSTPAS
P.puti A   LIKAHKGDRW GNLTYRKAAR NFGPIMAMAA KTAIAQVDQV VELGELDPEH IITPGIFVQR VVAVSGAAAS
H.pyl A    LIKAYKSDTL GNLVFRKTAR NFNPLCAMAA KICVAEVEEI VPAGELDPDE IHLPGIYVQH IYKGEKFEKR
B.subt     IVKAWKADTM GNLIFRKTAR NFNPIAAMAG KITIAEAEEI VEAGELDPDH IHTPGIYVQH VVLGASQEKR
Pig        LVKAWKADQA GNVTFRKSAR NFNLPMCKAA ETTVVEVEEI VDIGSFAPED IHIPKIYVHR LVKGEKYEKR 281                                               *                        350
E.coli                W MRNNVLAGVA QELRDGDIVN LGIGLPTMVA NYLPEGIHIT LQSENGFLGL
C.acet B       MINDKNL AKEIIAKRVA RELKNGQLVN LGVGLPTMVA DYIPKNFKIT FQSENGIVGM
A.calc A/B         MSYHKL TRDQIAQRVA QDIPEGSYVN LGIGLPTKIA SYLPADKDVF LHSENGLLAF
P.puti A/B AAP*    MTITKKL SRTEMAQRVA ADIQEGAYVN LGIGAPTLVA NYL.GDKEVF LHSENGLLGM
H.pyl A    SIAKAI*
H.pyl B    IEKITTRSAK*        MREAIIKRAA KELKEGMYVN LGIGLPTLVA NEVS.GMNIV FQSENGLLGI
B.subt     IEKRTVQQAS GKGEAK.MKE ARKRMVKRAV QEIKDGMNVN LGIGMPTLVA NEIPDGVHVM LQSENGLLGI
Pig        IERLSVRKEE DVKTRSGKLG VRERIIKRAA LEFEDGMYAN LGIGIPLLAS NFISPNMTVH LQSENGIILGL 351                                                                          420
E.coli     GP...VTTAH PDLVNAGGQP CGVLPGAAMF DSAMSFALIR GGHIDACVLG GLQVDEEANL ANWVVPGK.M
C.acet B   GASPKINEAD KDVVNAGGDY TTVLPDGTFP DSSVSFSLIR GGHVDVTVLG ALQVDEKGNI ANWIVPGK.M
A.calc B   GPPPAAGEED PELINAGKEY VTMLEGGCFP HHGDSFAMMR GGHLDICVLG AFQIAANGDL ANWHTGAPDA
P.puti B   GPSPAPGEED DDLINAGKQH VTLLTGAFF VTLLTGGAFP HHADSFSMMR GGHLDIAVLG AFQVSVKGDL ANWHTGAEGS
H.pyl B    GAYPLEGSVD ADLINAGKET VTVVPGASFP NSADSFAMIR GGHIDLAILG GMEVSQNGDL ANWMIPKK.L
B.subt     GPYPLEGTED ADLINAGKET ITEVTGASYF DSAESFAMIR GGHIDLAILG GMEVSECGDL ANWMIPGK.M
Pig        GPYPLQNEVD ADLINAGKET VTVLPGASYF SSDESFAMIR GGHVNLTMLG AMQVSKYGDL ANWMIPGK.L
```

FIG.2C

```
           421
E.coli     VPGMGGAMDL VTGSR.KVII AMEHCAKDGS AKILRRCTMP LTAQHAVHML VTELAVFRFI .DGKMWLTEI
C.acet B   LSGMGGAMDL VNGAK.KVII AMRHTNK.GQ PKILKKCTLP LTAKSQANLI VTELGVIEVI .NDGLLLTEI
A.calc B   IPSVGGAMDL AVGAK.KVFV TTDHVTKKGE PKIVAELTYP ATGQKCVDRI YTDLCIIDVV PEG.LKVIEK
P.puti B   IPAVGGAMDL ATGAR.QVFV MMDHLTKTGE SKLVPECTYP LTGIACVSRI YTDLAVLEVT PEG.LKVVEI
H.pyl B    IKGMGGAMDL VHGAK.KVIV IMEHCNKYGE SKVKKECSLP LTGKGVVHQL ITDLAVFEFS .NNAMKLVEL
B.subt     VKGMGGAMDL VNGAK.RIVV IMEHVNRHGE SKVKKTCSLP LTGQKVVHRL ITDLAVFDFV .NGRMTLTEL
Pig        VKGMGGAMDL VSSAKTKVVV HKIMEKCTLP TMEHSAKGNA LTGKQCVNRI ITEKAVFDVD RKKGLTLIEL 491                                                      521
E.coli     ADGCDLATVR AKTEARFEVA ADLNTQRGDL *
C.acet B   NKNTTIDEIR SLTAADLLIS NELRPMAV*
A.calc B   VEGLSFEELQ RLTGATLIDA TQG*
P.puti B   CADIDFDELQ KLSGVPLIK*
H.pyl B    QEGVSLDQVR EKTEAEFEVH L*
B.subt     QDGVTIEEVY EKTEADFAVS QSVLNS*
Pig        WEGLTVDDIK KSTGCDFAVS PKLIPMQQVT T*
```

COMPOSITIONS AND METHODS RELATING TO DRUG DISCOVERY AND DETECTION AND TREATMENT OF GASTROINTESTINAL DISEASES

This application claims the benefit of U.S. Provisional Application No. 60/014,906 filed Apr. 5, 1996.

INTRODUCTION

1. TECHNICAL FIELD

This invention provides for compositions and methods relating to enzymes in the poly-3-hydroxybutyrate metabolic pathway in bacteria that can propagate at low pH, such as *Helicobacter pylori*.

2. BACKGROUND

Safe, efficacious and cost effective methods for the treatment and diagnosis of peptic ulcers and gastritis continue to elude physicians. Traditionally ulcerogenesis was blamed on a myriad of factors, such as nervous tension, hot spicy foods, and hormonal imbalance. Bed rest and a bland diet were commonly prescribed along with drugs to neutralize the gastric acid and enzymes. The advent of $H_2$ antagonists and acid pump blockers decreased acid secretion in the stomach, but was not necessarily curative or cost effective.

More recently workers have investigated *Helicobacter pylori* (*Hp*), a spiral Gram-negative, microaerophilic bacterium, as a cause of ulcers due to *Hp* chronic infections of the human stomach. *Hp* has been identified as the causal agent of type B gastritis, peptic ulcers and gastric cancer (Cover et al., *ASM News* Vol. 61 No. 1 pp. 21–26 (1995)). At least sixteen other species of Helicobacter have been isolated from the stomachs or intestines of mammals and additional Helicobacter species are likely to be identified in the future. It is estimated that 40% of the population in developed countries and 80% of the population in underdeveloped countries have or have had *Hp* infections. If left untreated, the *Helicobacter pylori* infection can result in chronic gastritis and can persist for life.

*Hp* infection is also a significant predisposing factor in the development of peptic ulcer disease, gastric lymphoma, and gastric adenocarcinoma (*Journal of Clinical Investigation*, Vol. 94, p. 4–8 (1994)). Ten percent of individuals infected by *Hp* develop peptic ulcer disease. Atrophic gastritis is considered a risk factor for developing gastric adenocarcinoma, one of the most common and deadly neoplasms worldwide, and many studies have shown that *Hp* infection is associated with a 2.7- to 12-fold increased risk of developing this cancer. In addition, *Hp* infection has been implicated in 92% of patients with low-grade B-cell lymphomas of gastric mucosa-associated lymphoid tissue (MAL) and is also associated with gastric B-cell non-Hodgkin's non-MALT lymphomas. Although ulceration or cancer develops in only a small proportion of infected persons, early diagnosis and treatment of *Helicobacter pylori* infections can obviate the risk of developing such complications and can relieve gastritis. Physicians have found that antibiotics can relieve severe stomach inflammation and help heal gastric ulcers. The current treatment is based on a triple therapy, which involves adminstering two antibiotics and a acid pump inhibitor to reduce stomach acidity. This treatment, however, is costly, has side effects and in many countries of the third world, where infections are more prevalent, antibiotic resistant strains are emerging. In addition, most antibiotics have no effect in resting bacteria and there exists a need for a treatment effective against coccoid forms of *Helicobacter pylori*.

*Helicobacter pylori* attaches specifically to the gastric epithelia cells lining the antrum of the stomach and can remain in its niche for decades before its host exhibits any serious effects. Despite the importance of *Hp* as a pathogen, however, little is known about its metabolic and biosynthetic pathways, given their unusual evolutionary adaptations that enable *Hp* to live at low pH. In particular, the specific growth requirements of the bacterium are still unknown. Glucose metabolism by *H. pylori* has been the matter of some debate. Early studies indicated that sugars are not major substrates for the organism. Recently, studies established that *H. pylori* is indeed able to metabolize sugars via different pathways. However, the low rate and extent of glucose metabolism together with the fact that *H. pylori* growth during log phase is independent of the presence of glucose suggests that glucose is not an energy source for *H. pylori*. The investigation by Mendz et al. of pyruvate metabolism by *H. Pylori* under aerobic conditions yielded alanine, lactate, acetate, formate and succinate (*Arch. Microbiol.* 162:187–192 (1994)). Mendz et al. suggested the incorporation of the pyruvate carbon skeleton into the Kreb's cycle. In contrast, from a similar study, Chalk et al. concluded that the major aerobic oxidation product of pyruvate was acetate and found no evidence of Kreb's cycle activity (*Microbiology* 140:2085–2092 (1994)). Recently, researchers have concluded that this bacterium can survive employing amino acids as basic nutrients, with acetate, formate and succinate being the principal catabolic products (Mendz et al., *Int. J. Biochem. Cell Biol.* 27:1085–1093 (1995)). Information about the metabolism and substrate utilization by *Hp* is useful for understanding bacterial colonization and survival and to design methods for early detection of *Hp* infection as well as to develop new drugs to treat infection.

In view of the role for *Helicobacter pylori* in gastric disease states and the paucity of understanding of *Helicobacter pylori* and other bacteria that reside at low pH's, there exists a need in the art for compounds and methods for detection and treatment of gastric disease caused by bacteria and methods to identify these and related compositions. Further, such compositions can serve as commercial research reagents for studying *Hp* metabolic and synthetic pathways. Because there has been little progress in developing a more defined model of the molecular mechanisms underlying *Helicobacter pylori* infection, few significant therapeutic methods applicable to treating gastric disease beyond conventional therapies have emerged. Although a minor metabolic pathway in other bacteria, the *Helicobacter pylori* poly-3-hydroxybutyrate metabolic pathway is identified herein for the first time as being essential for *Helicobacter pylori* survival. Enzymes in this pathway can be exploited for the detection or prevention of potential disease states, as well as the discovery of novel agents for the treatment of certain gastric diseases. These and other objects are provided by the invention.

SUMMARY OF THE INVENTION

The invention provides a poly-3-hydroxybutyrate metabolic pathway essential for *Helicobacter pylori* survival in a host. The invention provides isolated polynucleotides comprising nucleic acid sequences encoding a novel *Helicobacter pylori* CoA-transferase protein (*Hp* CoA-t). The invention provides isolated polynucleotides having nucleic acid sequences encoding *Hp* CoA-t, preferably as the coding region described in FIG. 1A and FIG. 1B (SEQ ID NO.: 01), nucleic acid sequences complementary to that sequence, nucleic acid sequences containing degenerate codon replacements within the *Helicobacter pylori* CoA-t coding region of that sequence, allelic variants of that sequence, closely related variants having at least 85% homology to that sequence, and fragments at least 10 bases in length from those sequences and which will selectively hybridize to nucleic acids encoding Hp CoA-t. The nucleic acids sequences are preferably those found in nature, although in view of this invention the polynucleotides containing these sequence can be prepared in numerous ways known in the art, including synthetic methods. Also provided are Hp CoA-t recombinant constructs, e.g. fusions, truncations, substitutions, that provide polypeptides having certain desirable properties such as constitutive 3-oxoacid CoA-transferase activity, antigenicity, and ease of purification and identification.

The invention also provides isolated polynucleotides comprising nucleic acid sequences encoding a portion of a novel *Helicobacter pylori* thiolase, described in Table 1 (SEQ ID NO.:16), nucleic acid sequences complementary to that sequence and polynucleotides at least 85% homologous to SEQ ID NO.:16.

Also provided are isolated and purified Hp CoA-t and thiolase polypeptides containing the sequences found in the polynucleotides of the invention. Methods for preparation of Hp CoA-t and thiolase polypeptides are provided, including isolation from natural sources, synthetic production, and recombinant production using the nucleic acid sequences provided by the invention. The invention provides an Hp CoA-t protein, and fragments thereof, having an amino acid sequence depicted in FIGS. 1A and 1B (SEQ ID NO.:02 and SEQ ID NO.:03). Peptides of the invention can also be used to generate antibodies for detection assays.

The invention includes vectors and transformed host cells for expressing the isolated polynucleotides of the invention when the isolated polynucleotides are operably linked to an expression vector appropriate for expression in the host cell used.

The isolated polynucleotides of the invention can find further use in the dissection of CoA-related metabolic pathways of Hp and in antisense treatment for some Hp-related gastric diseases.

The invention also provides compositions and methods to screen libraries of agents for their ability to inhibit the properties of Hp CoA-t, which as disclosed herein include its 3-oxoacid-CoA-transferase activity and to a lesser extent its 3-oxoadipate-CoA-transferase and butyrate-acetoacetate-CoA-transferase activities. The invention further provides compositions and methods to screen libraries of agents for their ability to inhibit the properties of Hp thiolase and Hp synthase. The invention provides compositions and methods for treating or preventing gastritis, peptic ulcer disease, and gastric cancer in human and veterinary patients, compositions and methods for screening a library of agents for pharmacological activity in inhibiting CoA-transferase, thiolase and PHB synthase activities. The present invention is also directed to pharmaceutical compositions for the control of Helicobacter-dependent diseases in mammals which includes an agent capable of inhibiting CoA-transferase, thiolase or PHB synthase and to a method of controlling Helicobacter-dependent diseases which includes administering to a mammal suffering from a Helicobacter-dependent disease an agent capable of inhibiting Helicobacter CoA-transferase, thiolase or PHB synthase.

BRIEF DESCRIPTION OF THE DRAWINGS

FIGS. 1A and 1B show the nucleotide sequence and amino acid sequences of the Hp CoA-t subunits A and B. Transcriptional start sites and potential ribosomal binding sites are underlined. The first methionine of each subunits is in bold. Stop codons are indicated with bold asterisks.

FIGS. 2A, 2B and 2C show an alignment of the deduced amino acid sequences of the CoA-transferase subunits A and B of *E. coli*, *C. acetobutylicum* (*C. acet*) (Cary et al., *Appl Environ Microbiol* 56:1576–1583 (1990), *A. calcoaceticus* (*A. calc*) (Shanley et al., *Gene* 138:59–65 (1994)), *P. putida* (*P. puti*) (Parales et al., *J. Bacteriol* 174:4657–4666 (1992)) with the two subunits of *H. pylori* (*H. pyl*) and the monomeric proteins from *B. subtilis* (*B. subt*) and pig heart mitochondrium (Pig) (Lin et al., *J. Biol Chem* 267:975–978 (1992)). Identical residues among all aligned proteins are in bold type. The cluster of each protein is underlined. The conserved active site glutamate is indicated with a bold asterisk above the sequence. Numbers are referred to the amino acid residues of the mitochondrial 3-oxoacid CoA-transferase of pig heart.

7A) 3-oxoadipate CoA-t activity measured as appearance of β-adipyl CoA from β-ketoadipate+succinyl CoA at 305 nm in 100 µl of CL. (FIG. 7B) Acetoacetate CoA-t activity measured as disappearance of acetoacetyl CoA at 310 nm in 50 µl of CL. (FIG. 7C) 3-oxoacid CoA-t activity measured as formation of acetoacetyl CoA from acetoacetate+succinyl CoA at 310 nm in 50 µl of CL of cells transfected with pUreA and 0.5 µl of cells transfected with pCoA-t.

DESCRIPTION OF SPECIFIC EMBODIMENTS

DEFINITIONS

Figure 3:
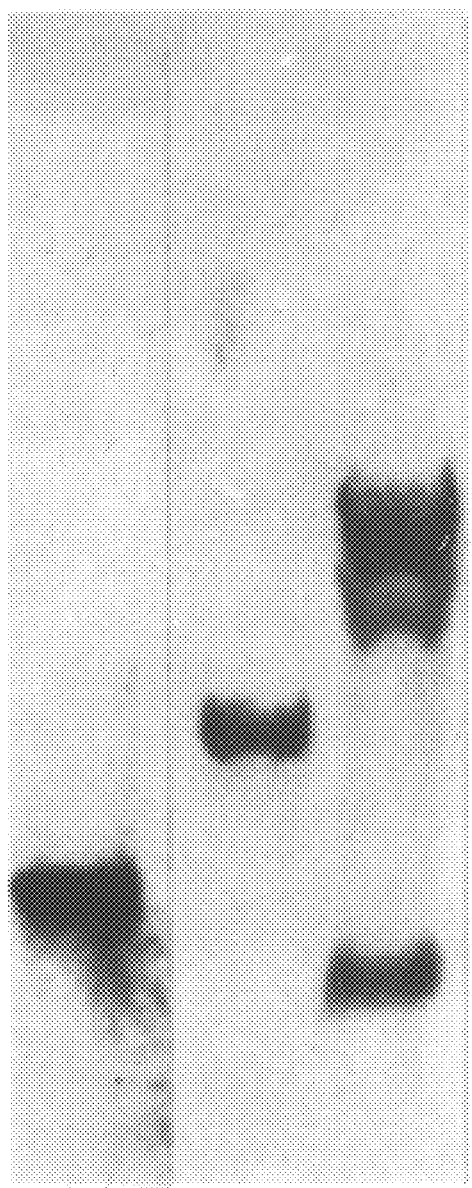
FIG. 3 shows a Southern blot analysis of *Helicobacter pylori* (*Hp*) genomic DNA. Hp DNA from two sources was digested with HaeIII and separated by electrophoresis in 0.7% agarose. After transfer, membranes were hybridized with the ECL-labeled 1000 base pairs PCR-generated probe described in Example 1 at 37° C. in DIG Easy Hyb solution and washed using high stringency conditions (0.1× SSC, 0.1% SDS, 68° C.). Lane 1:10 ng of purified 1000 base pairs PCR-generated probe; lane 2:10 μg of NCTC Hp 11637; lane 3: Hp 69A. Molecular marker sizes in bp are indicated next to the panel (ECL-labeled λ/HindIII, Amersham).

Generally, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, $CaCl_2$-mediated transformation). Generally, enzymatic reactions and purification steps supplied by manufacturers are performed according to the manufacturer's specifications. The techniques and procedures are generally performed according to conventional methods in the art and various general references (See generally, Sambrook et al. *Molecular Cloning: A Laboratory Manual*, 2d ed. (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described below are those well known and commonly employed in the art. Standard techniques can be used for chemical syntheses, chemical analyses, pharmaceutical formulation and delivery, and treatment of patients. As employed throughout the disclosure, the following terms, unless otherwise indicated, shall be understood to have the following meanings:

The term "isolated polynucleotide" referred to herein means a polynucleotide that has been subjected to manipulation, such that the isolated polynucleotide is no longer associated with the chromosome or cell that the polynucleotide is normally associated with in nature, such as a polynucleotide of genomic, recombinant, or synthetic origin or some combination thereof.

The term "isolated protein" referred to herein means a protein that is no longer associated with the cell that the protein is normally associated with in nature, such as (1) a protein free of other proteins from the same source, e.g. free of Helicobacter proteins, (2) a protein expressed by a cell from a different species, (3) a protein that does not occur in nature and (4) a protein produced from cDNA, recombinant RNA, or synthetic origin or some combination thereof.

The term "polypeptide" is used herein as a generic term to refer to native protein, fragments, or analogs of a polypeptide sequence. Hence, native protein, fragments, and analogs are species of the polypeptide genus. Preferred CoA-transferase polypeptides include: the full-length *Hp* CoA-transferase protein comprising Subunit A & Subunit B, which comprise the polypeptide sequence in FIGS. 1A and 1B (SEQ ID NO.:02 and SEQ ID NO.:03); polypeptides comprising Subunit A alone or Subunit B alone; polypeptides comprising an amino acid sequence less than 30% homologous to non-Helicobacter CoA-transferases; polypeptides comprising a CoA-transferase domain essential for enzymatic activity, a domain that comprises the CoA acceptor site, in whole or in part, a domain that comprises the CoA donor site, in whole or in part; and polypeptides comprising the amino acid sequence of any region of CoA-transferase that interfere with the enzymatic activity of CoA-t, directly or indirectly (e.g. by altering the structure of the CoA-t) or that provide antigenic sequences for making antibodies, provided that the polypeptides are less than 70% homologous to non-Helicobacter CoA-t and are at least 80% homologous to SEQ ID No.:2 or SEQ ID No.:3, preferably at least 85% homologous, more preferably at least 90% homologous, and most preferably more than 95% homologous.

The term "naturally-occurring" as used herein as applied to an object refers to an object can be found in nature. For example, a polypeptide or polynucleotide sequence that is present in an organism (including viruses) that can be isolated from a source in nature and which has not been intentionally modified by man in the laboratory is naturally-occurring.

The term "operably linked" referred to herein refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The term "control sequence" referred to herein refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and can also include additional components whose presence is advantageous, for example, leader sequences and fusion partner sequences.

The term "in tandem" as referred to herein refers to the location of genes encoding enzymes in the poly-3-hydroxybutyrate metabolic pathway. Genes are located "in tandem" when they are clustered in a particular region on the bacterial chromosome. In bacteria, genes encoding proteins involved in a particular enzymatic pathway will often be clustered in a particular region on the bacterial chromosome. Sometimes such genes will be present on a single operon, i.e. under the control of a single promoter. Often such genes will be clustered together but will be under the control of separate promoters. Genes that are clustered in a particular region are closely linked, separated by less than 4 Kb of nucleic acid sequence, preferably separated by less than 2 Kb, and most preferably separated by less than 1 Kb. For example, and not by way of limitation, the *Hp* CoA-transferase and thiolase genes are separated by approximately 1000 base pairs and thus are said to be located "in tandem".

The term "polynucleotide" as referred to herein means a polymeric form of nucleotides of at least 10 bases in length, either ribonucleotides or deoxynucleotides or a modified form of either type of nucleotide. The term includes single- and double-stranded forms of DNA.

The term "oligonucleotide" referred to herein includes naturally occurring, and modified nucleotides linked together by naturally occurring, and non-naturally occurring oligonucleotide linkages. Oligonucleotides are usually a polynucleotide subset with 200 bases or fewer in length. Preferably oligonucleotides are minimally 10 to 60 bases in length and most preferably 12, 13, 14, 15, 16, 17, 18, 19, or 20 to 40 bases in minimal length. Oligonucleotides are usually single-stranded, e.g. for probes; although oligonucleotides may be double-stranded, e.g. for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. An oligonucleotide can include a label for detection, if desired.

The term "sequence homology" referred to herein describes the proportion of base matches between two nucleic acid sequences or the proportion amino acid matches between two amino acid sequences, i.e. the degree of identity between two nucleotide sequences. When sequence homology is expressed as a percentage, e.g., 50%, the percentage denotes the proportion of matches over the length of sequence from Hp CoA-t that is compared to some other sequence. When using GAP or BESTFIT computer alignment programs, discussed in greater detail below, gaps (in either of the two sequences) are permitted to maximize matching; gap lengths of 15 bases or less are usually used, 6 bases or less are preferred with 2 bases or less more preferred. When using oligonucleotides as probes or in treatments the sequence homology between the target nucleic acid and the oligonucleotide sequence is generally not less than 17 target base matches out of 20 possible oligonucleotide base pair matches (85%); preferably not less than 9 matches out of 10 possible base pair to matches (90%), and most preferably not less than 19 matches out of 20 possible base pair matches (95%).

The term "selectively hybridize" referred to herein means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions whereby only nucleic acid sequences having a substantial identity of greater than 95% with respect to each other will hybridize. Alternatively, stringency can be varied to achieve selective hybridization conditions whereby nucleic acid sequences having homology less than 95% with respect to each other will hybridize. These conditions are known in the art and discussed herein and examples are provided. Generally, the nucleic acid sequence homology between the polynucleotides, oligonucleotides, and fragments of the invention and a nucleic acid sequence of interest will be at least 85%, and more typically with preferably increasing homologies of at least 90%, 95%, 99%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 750 using the program BLASTP 1.4.8MP (Altschul. et al., *J. Mol. Biol.* 215:403–410 (1990)) on the following databases: Non-redundant PDB+SwissProt+SPupdate+PIR+GenPept+GPupdate.

As applied to polynucleotides, the term "substantial identity" means that two nucleic acid sequences when optimally aligned such as by the programs BLAST (Altschul et al., *J. Mol. Biol.* 215:403–410 (1990)), FASTA (Pearson and Lipman, *Proc. Natl. Acad. Sci. USA* 85:2444–2448 (1988)), GAP (Needleman and Wunsch, *J. Mol. Biol.* 48:443–453 (1970)), or BESTFIT (Smith and Waterman, *Advances in Applied Mathematics* 2:482–489 (1981)) share at least 85%, preferably at least 90% sequence homology and most preferably greater than 95% sequence homology. Preferably, bases which are not identical nevertheless are part of a degenerate codon that encodes the same amino acid at that amino acid position. Alternatively, bases which are not identical preferably are part of a degenerate codon that encodes a conservative amino acid substitution for that amino acid position.

As applied to polypeptides, the term "substantial identity" means that two peptide sequences when optimally aligned, such as by the programs GAP or BESTFIT using default gap weights, share at least 80 percent sequence homology, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

The term "degenerate codon" referred to here means any of the nucleotide codon triplets encoding a desired amino acid according to the genetic code. Codons can be selected based upon known preferred codon usage in a host organism such as *E. coli*.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length DNA sequence (e.g., the DNA sequence shown in FIGS. 1A and 1B). Fragments typically are at least 5, 6, 8 or 10 amino acids long, preferably at least 14 amino acids long, more preferably at least 20 amino acids long, usually at least 50 amino acids long, and even more preferably at least 70 amino acids long.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential stearic hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "compound" as used herein preferably refers to a peptidic, peptidomimetic, organic, or other chemical molecule and also refers to a nucleic acid molecule or chemical derivative thereof. The compound can interact with, or be, the polynucleotides or polypeptides of the invention.

The term "pharmaceutical agent" or "drug" as used herein refers to a chemical compound or composition capable of inducing a desired therapeutic effect when properly administered to a patient or other organism.

The headings provided herein describe the general topic discussed and are not intended to be exclusive of information discussed in other sections. Frequently, information, methods, compositions, and other aspects may be applicable to more than one embodiment of the invention and can be so combined.

INTRODUCTION

The invention provides for novel enzymes in a poly-3-hydroxybutyrate metabolic pathway essential for the survival of a bacterium that can propagate at low pH in a mammalian stomach, liver or intestine. The invention provides for novel CoA-transferase polynucleotides termed CoA-t, and novel thiolase polynucleotides not heretofore recognized or known in the art. The invention also provides diagnostic and therapeutic uses for such polynucleotides and their protein products. The CoA-transferase was originally found in *Helicobacter pylori*. Sequencing of the clone obtained by random amplification by polymerase chain reaction of *Hp* 69A chromosomal DNA led to the identification of a *Hp* genomic DNA fragment containing a specific sequence of 1395 nucleotides in length (SEQ ID NO.:01— See Table 2). Computer analysis of DNA sequence revealed two open reading frames designated as ORF1 and ORF2 (FIGS. 1A and 1B). The largest open reading frame, ORF1, begins at nucleotide 49, terminates at nucleotide 771 and potentially encodes a polypeptide of 240 amino acids. The other one, ORF2, located downstream, extends from nucleotide 734 to nucleotide 1390 and potentially encodes a polypeptide of 219 amino acids. Both ORFs are oriented in the same direction, and the stop codon of ORF1 (TGA) overlaps with the methionine codon of ORF2. Both ORFs are preceded by putative ribosome binding sites (Shine-Dalgarno sequence shown as AGGA). ORF1 and ORF2 encode Subunits A and B, respectively, of *Hp* CoA-transferase.

CoA-transferases are enzymes catalyzing the reversible transfer of Coenzyme A (CoA) from one carboxylic acid to another. CoA-transferases have been identified in many procaryotes. In bacteria, carboxylic acids are activated by the addition of CoA before they are further metabolized and used as carbon and energy sources. A similar metabolic route occurs in mammals under conditions of starvation or diabetes, when glucose levels are low or unusable, ketone bodies are released from the liver and provide major source of metabolic energy for certain tissues, including the brain, heart and kidney.

A 3-oxoadipate CoA-transferase carries out the penultimate step in the conversion of benzoate and 4-hydroxybenzoate to tricarboxylic acid cycle intermediates in bacteria utilizing the β-ketoadipate pathway. A butyrate-acetoacetate CoA-transferase acts mainly to detoxify the medium by removing the acetate and butyrate excreted earlier in the fermentation. This enzyme has therefore a role fundamentally different from other CoA-transferases, usually involved in the uptake of substrates for energy and structural use (Wiesenborn et al.). A 3-oxoacid CoA-transferase is responsible for the formation of acetyl CoA by transfer of a CoA moiety from succinyl-CoA to acetoacetate (White et al. 1976 *Journal of Biological. Chemistry*. 251:1708–1711). The enzyme is important for ketone bodies to serve as fuels in energy metabolism.

In the case of *Hp*, CoA-t is able to convert very efficiently acetoacetate into acetoacetyl CoA in the presence of succinyl CoA. The enzyme is made constitutively in *Hp* when the bacteria are grown in vitro in plates or in liquid cultures. Although other CoA-transferases are present in *E. coli*, no 3-oxoacid activity was detected in these bacteria, an observation that permits a method for the selective identification of the presence of bacteria that reside at low pH, such as *Helicobacter pylori*.

Novel compositions comprising isolated polynucleotides and oligonucleotides having nucleic acid sequences homologous to *Hp* CoA-transferase are provided by the invention. Isolated proteins encoded by these polynucleotides are also provided by the invention. Exemplary nucleic acid and amino acid sequences are set forth in SEQ ID NOS:01–03.

Identification and characterization of the CoA-transferase led to the identification of a partial sequence of a *Helicobacter pylori* thiolase located approximately 700 base pairs 5' of the nucleic acid sequence of CoA-transferase. 3-ketothiolases, sometimes referred to as acetoacetyl-CoA C-acetyl transferases, are enzymes that participate in the condensation of two molecules of acetyl CoA to produce acetoacetyl CoA. These enzymes can also catalyze the reverse reaction, i.e., the cleavage of acetoacetyl CoA to two acetyl CoA moieties. When characterizing the activity of CoA-transferase, the inventor found that accumulation of acetoacetyl CoA produced by CoA-transferase could be enhanced by inhibiting the *Hp* thiolase activity by the addition of iodoacetamide. Thus, the invention also provides for the existence of the gene and the activity of the *Hp* thiolase.

Because the CoA-transferase and thiolase sequences are closely linked, these and other genes encoding enzymes in the poly-3-hydroxybutyrate (PHB) metabolic pathway are probably located in tandem as are, for example, the corresponding genes for enzymes in the metabolic pathway of *Alcaligenes eutrophus* (Steinbuchel et al., Molecular Microbiology (1991) 5:535–542). Polyhydroxyalkanoates (PHAs) are polyesters of various 3-, 4- and 5-hydroxyalkanoic acids that are accumulated by a large number of bacteria as carbon and energy-storage compounds during nutrient-limited conditions. The three-step pathway for the biosynthesis of PHB in *Alcaligenes eutrophus* is present in the majority of PHB-accumulating bacteria. The three enzymes involved are: a 3-ketothiolase (EC 2.3.1.9), a NADPH-dependent acetoacetyl CoA reductase (EC 1.1.1.36) and a PHB synthase (no EC number assigned). The degradative part of the PHB cycle is less clear. Degradation probably involves oxidation of 3-hydroxybutyrate to acetoacetate, which is converted to acetyl CoA in two steps by the enzymes: CoA transferase (EC 2.8.3.5) and the degradative counter part of 3-ketothiolase. PHB storage granules has been described in some species of the genus Spirullum and has also been observed in *Gastrospirillum suis* (*Helicobacter heilmannii*) found in pig stomachs (Mendez et al., 1990).

The inventor has also observed by electron microscopy PHB-like granules in the cytoplasm of *H. pylori* present in gastric biopsies of infected patients and has, by Southern blot analysis using probes corresponding to a highly conserved region of PHA synthases, identified the presence of a *H. pylori* PHA synthase gene. Several of the compositions and methods of the invention are predicated on this discovery that *H. pylori* uses PHB or other PHA(s) as storage material and therefore possesses all the enzymatic machinery implicated in the synthesis and degradation of the polyester. Thus, all the enzymes in the PHB metabolic pathway are targets for diagnostics and drug therapies leading to the eradication of *Helicobacter pylori* infection.

Accordingly, the invention also provides methods for detecting the presence of absence of Helicobacter in a sample using probes hybridizable to polynucleotides encoding for CoA-transferase or thiolase or using antibodies recognizing CoA-transferase or thiolase, methods for identifying a potential drug candidate for the treatment of certain gastric diseases by observing the effect of such drug candidates on CoA-transferase, thiolase, or PHB synthase activities, inhibitors of such activities, and methods for treating certain gastric diseases by administering such inhibitors.

POLYNUCLEOTIDES

In one embodiment, the invention provides for polynucleotides and oligonucleotides at least ten bases in length to the nucleic acid sequence or the complementary nucleic acid sequence of an enzyme in a poly-3-hydroxybutyrate metabolic pathway, which enzyme is encoded by polynucleotides from bacteria that can propagate in low pH and in a mammalian stomach, liver or intestine. These polynucleotides and oligonucleotides can be hybridizable under high stringency conditions having at least 85% nucleic acid identity (with preferably increasing identity to 100%) to the nucleic acid sequences identified herein. For example, the polynucleotides and oligonucleotides can be hybridizable to the nucleic acid sequence of SEQ ID NO.: 1 or its complement and can encode a CoA-transferase in whole, or in part. As a further example, the polynucleotides and oligonucleotides can be hybridizable to the nucleic acid sequence of SEQ ID NO.: 16 (Table 1) or its complement and can encode a thiolase in part. Usually, such polynucleotides and oligonucleotides hybridizable to the nucleic acid sequence of SEQ ID NO.: 1 have at most 80% homology to a non-*Hp* CoA-transferase nucleic acid sequence, such as, for example, the nucleic sequences of the polynucleotides encoding for the CoA-transferase subunits of *E. coli, C. acetobutylicum, A. calcoaceticus, P. putida*, or the monomeric proteins from *B. subtilis* or pig heart mitochondrium. Similarly, polynucleotides and oligonucleotides hybridizable to the nucleic acid sequence of SEQ ID NO.: 16 have at most 80% homology to a non-*Hp* thiolase nucleic acid sequence, such as, for example, the nucleic acid sequences of the polynucleotides encoding for the thiolases of *A. calcoaceticus, E. coli, C. acetobutylicum, A. eutrophus, C. sativus* or the rat or human peroxisomal or mitochoncrial thiolase proteins or the elastin like protein of *Drosophila melanogaster*.

TABLE 1

Nucleic acid sequence of *H. pylori* thiolase polynucleotide fragment

```
  1 GAATTCATCA GGGATCAATG ATGGCGCGAG CATTATCATT TTATGCAGCG   (SEQ ID NO.:16)
 51 CTAAAAAAGC GCAAAAATTA GGGTTAAAAG CCATGGCTAC TATCAGGGGG
101 TTTGGTTTGG GTGGTTGCAG TCCGGATATA ATGGGTATAT GCCCTAGTAT
151 TGCGATTAAA AACAATCTTA AAAATGTCAA AATGAATCTC AATGACATCA
201 ATCTTTTTGA ACTCAATGAA GCCTTTGCCG CGCAAAGTCT AGCCGTGTTA
251 AAAGAGCTTG AATTAAACCC CAATATAGTG AATGTGAATG GAGGCGCGAT
301 A
```

Often the polynucleotides of the invention will comprise (1) the entire coding region of *Hp* CoA-transferase ($A^{73}$TGAA to TATAG$^{1394}$ of SEQ ID NO.:01), (2) the coding region of either Subunit A or Subunit B alone ($A^{73}$TGAA to TATAG$^{774}$ or $A^{771}$TGAG to TATAG$^{1394}$ of SEQ ID NO.:01, respectively), (3) any sequence complementary to (1) or (2), (4) a nucleic acid sequence that is hybridizable with the sequence of SEQ ID NO.:01 or its complement, (5) the entire nucleic acid sequence of SEQ ID NO.:16, (6) any sequence complementary to (5), (6) the entire coding region of *Hp* thiolase, or (7) a nucleic acid sequence that is hybridizable with the sequence of SEQ ID NO.:16 or its complement. The entire coding region of *Hp* thiolase can be isolated by probing *Hp* DNA with a polynucleotide having the nucleic acid sequence of SEQ ID NO.:16 and employing standard nucleic acid sequencing techniques to identify an open reading frame corresponding to the full length thiolase gene. The polynucleotides of the invention are particularly useful as probes for performing selective, high stringency hybridization to determine the presence or absence of *Hp* CoA-transferase or thiolase nucleic acid in a sample (See Example 4) and for isolating a naturally occurring nucleic acid encoding for *Hp* CoA-transferase or thiolase.

Some polynucleotides of the invention are included in Table 2.

identify clones that bind to both probes under hybridization and wash conditions. Oligonucleotides can be synthesized

TABLE 2

| SEQ ID NO | Description | Primer Name | Sequence |
|---|---|---|---|
| 1 | 1395 base pairs *Hp* genomic DNA fragment | — | nucleic acid |
| 2 | Subunit A of *Hp* CoA-transferase | — | amino acid |
| 3 | Subunit B of *Hp* CoA-transferase | — | amino acid |
| 4 | 5'-GATAAACCGGCACC-3' | 1CT14 | nucleic acid |
| 5 | 5'-GCGGGCGCGTCGTT-3' | 1CT20 | nucleic acid |
| 6 | 5'GGAATTCATGAACAAGGTTATAACCG-3' | 1CT42 | nucleic acid |
| 7 | 5'-GGAATTCTGCAGCTATAGGTGCACTTCAAATTCG-3' | 1CT43 | nucleic acid |
| 8 | 5'-GCTCTAGAGCCTCTCATTTCGCGCTCCTTGTCG-3' | 1CT32 | nucleic acid |
| 9 | 5'-CCATCGATATCACGACAAGGAGCGCGAAATGA-3' | 1CT31 | nucleic acid |
| 10 | 5'-CGGGATCCCGATGAACAAGGTTATAACCG-3' | 1CT45 | nucleic acid |
| 11 | 5'-GGAATTCGTCGACGCTATAGGTGCACTTCAAATTCG-3' | 1CT48 | nucleic acid |
| 12 | 5'-GCTCTAGAGCGATAAAACCGGCACC-3' | 1CT21 | nucleic acid |
| 13 | 5'-CCATCGATGGGCGGGCGCGTCGTT-3' | 1CT22 | nucleic acid |
| 14 | 5'-GGAATTCGTCGACTCTCATTTCGCGCTCCTTGTCG-3' | 1CT46 | nucleic acid |
| 15 | 5'-CGGGATCCCGATGAGAGAGGCTATCATTAAAAG-3' | 1CT48 | nucleic acid |
| 16 | 301 base pairs *Hp* genominc thiolase DNA fragment | — | nucleic acid |
| 17 | 100 amino acid *Hp* thiolase peptide fragment | — | amino acid |

Polynucleotides encoding naturally occurring CoA-transferase or thiolase can be isolated from *Helicobacter pylori* and other bacteria residing in low pH or in the intestine or the liver by the methods described herein, such as in Examples 1 and 2. Alternatively, such naturally occurring polynucleotides can be isolated by using polynucleotides or oligonucleotides comprising various other regions of the sequence of SEQ ID NO.:1 or SEQ ID NO.:16 and by implementing other molecular biology techniques known in the art.

Regions of SEQ ID NO.:1 or SEQ ID NO.:16 that share less than 80% nucleotide sequence identity with polynucleotides of mammalian CoA-transferase or thiolase, respectively, are desirable for this purpose.

Preferably polynucleotides are used as probes under high stringency wash conditions and with corresponding hybridization conditions, as known in the art. In addition, isolated polynucleotides can be used to make probes that are 50 base pairs to the full length of the *Hp* CoA-t or thiolase genes. Preferably probes are made from isolated polynucleotides 100–400 nucleotides in length, and most preferably probes are made from the entire coding region of the *Hp* CoA-t or thiolase genes.

Alternatively, oligonucleotides can be employed as probes. Techniques for using oligonucleotides as probes to detect the same or related nucleic acid sequences is well known in the art, see for example Sambrook et al, especially Chapter 11, the text of which is herein incorporated by reference. Usually, probes can be made from oligonucleotides that are 10 to 200 bases in length. Preferably probes are made from oligonucleotides 10 to 60 nucleotides in length and most preferably 12 to 40 bases in length. Specific probes can be designed based on results obtained using nucleic acid homology computer programs such as FASTA, which uses the method of Pearson and Lipman (*Proc. Natl. Acad. Sci. USA* 85:2444–2448 (1988)). The size of the probe is dependent upon the region of the gene to which it will be hybridized. The size of the probe increases as the degree of homology to undesirable nucleic acid sequences increases. In some instances a probe 10 nucleotides in length can be used, but in other instances probes at least 20 nucleotides and preferably 30 nucleotides will be used. To decrease the number of false positives, preferably two probes are used to on an Applied BioSystems oligonucleotide synthesizer according to specifications provided by the manufacturer.

Typically, hybridization and washing conditions are performed at according to conventional hybridization procedures. Typical hybridization conditions for screening plaque lifts (Benton and Davis (1978) *Science* 196: 180) can be: 50% formamide, 5×SSC or SSPE, 1–5×Denhardt's solution, 0.1–1% SDS, 100–200 µg sheared heterologous DNA or tRNA, 0–10% dextran sulfate, $1 \times 10^5$ to $1 \times 10^7$ cpm/ml of denatured probe with a specific activity of about $1 \times 10^8$ cpm/µg, and incubation at 42° C. for about 6–36 hours. Prehybridization conditions are essentially identical except that probe is not included and incubation time is typically reduced. Washing conditions are typically 1–3×SSC, 0.1–1% SDS, 50–70° C. with change of wash solution at about 5–30 minutes. Cognate bacterial sequences, including allelic sequences, can be obtained in this manner. For high stringency hybridization conditions, various parameters can be altered to increase the stringency of hybridization, such as by increasing the temperature of incubation with the labelled probe. Preferably, for greater flexibility in experimental design, the probe can be hybridized at a lower temperature, such as, for example, room temperature and the stringency can then be modified by altering the salt concentration and temperature of the wash solutions. For high stringency a wash temperature of greater than or equal to 42° can be used, such as, for example, 68°, in a wash buffer having a salt concentration less than 3× SSC, such as, for example, 0.1× SSC. In some cases, TMACL can also be used, particularly for polynucleotides rich in G-C base pairs in order to decrease non-specific binding. For a lower stringency wash, that can be used to hybridize polynucleotides with lower homologies or polynucleotides that are less than 60 base pairs in length temperatures of less than or equal to 42° can be used in a wash buffer having a salt concentration of greater than or equal to 2× SSC.

The invention includes methods for amplification of target nucleic acids, which can be used in hybridization assays, such as the polymerase chain reaction ("PCR") or PCR technique. The PCR technique can be applied to detect nucleotide sequences in suspected samples using oligonucleotide primers spaced apart from each other and based on the genetic sequence set forth herein. The primers are complementary to opposite strands of a double-stranded DNA molecule and are typically separated by from about 50 to 450 nucleotides or more (usually not more than 2000 nucleotides). This method entails preparing the specific oligonucleotide primers followed by repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula 2n where n is the number of cycles. Given that the average efficiency per cycle ranges from about 65% to 85%, 25 cycles produce from 0.3 to 4.8 million copies of the target sequence. The PCR method is described in a number of publications, including Saiki et al., *Science* (1985) 230:1350–1354; Saiki et al., *Nature* (1986) 324:163–166; and Scharf et al., *Science* (1986) 233:1076–1078. Also see U.S. Pat. Nos. 4,683,194; 4,683, 195; and 4,683,202, the text of each patent is herein incorporated by reference. Additional methods for PCR amplification are described in: PCR Technology: Principles and Applications for DNA Amplification ed. H A Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17, and; *PCR*, eds. McPherson, Quirkes, and Taylor, IRL Press, Oxford, all of which are incorporated herein by reference.

The polynucleotide or oligonucleotide can also comprise a fragment corresponding to or hybridizable under high stringency conditions to the coding region of either CoA-t subunit, or a complementary sequence thereof. Such a polynucleotide or oligonucleotide can also be used for performing selective, high stringency hybridization and is particularly useful for performing amplification of nucleic acid by polymerase chain reaction (PCR) to determine the presence or absence of Hp CoA-transferase nucleic acid in a sample (See Example 3) and for isolating a naturally occurring nucleic acid encoding for Hp CoA-transferase (See Example 1).

In one aspect the polynucleotides oligonucleotides of the invention can exist in linear form, such as, for example, the polynucleotides shown in Table 2. In another aspect the polynucleotides can exist in circular form as part of a plasmid, such as, for example, the polynucleotides shown in Table 3.

TABLE 3

| Plasmid | Polynucleotide Fragment of SEQ ID NO.:1 | Parental Vector | Cloning Sites | Host Cell |
|---|---|---|---|---|
| pGB7 | nucleotides 1–993 of SEQ ID NO.:1 | pBluescript KS (Stratagene) | ClaI, XbaI | *E. coli* X11 blue |
| pbsK-OxoA | nucleotides 1–777 of SEQ ID NO.:1 | pBluescript SK (Stratagene) | ClaI, XbaI | *E. coli* X11 blue |
| pDB4 | nucleotides 73–777 of SEQ ID NO.:1 | pQE11 (Diagen) with his tag | BamHI, SalI | *E. coli* M15 |
| pDB5 | nucleotides 771–1394 of SEQ ID NO.:1 | pQE11 (Diagen) with his tag | BamHI, SalI | *E. coli* M15 |

TABLE 3-continued

| Plasmid | Polynucleotide Fragment of SEQ ID NO.:1 | Parental Vector | Cloning Sites | Host Cell |
|---|---|---|---|---|
| pCoAT | nucleotides 73–1394 of SEQ ID NO.:1 | pKK223-3 (Pharmacia) | EcoRI, PstI | *E. coli* JM105 |
| pUreA | negative control with a urease insert | pKK223-3 (Pharmacia) | | *E. coli* JM105 |

In another preferred aspect, the probe comprises a group of polynucleotide or oligonucleotide species containing different degenerate codons at various positions, which polynucleotides encode thiolase or Subunit A or Subunit B of CoA-transferase, in whole or in part, or both. Such polynucleotides or oligonucleotides can be useful for isolating nucleic acid sequences encoding polypeptides having an amino acid sequence 80% homologous to the amino acid sequence of Hp thiolase or CoA-transferase as determined by BLAST homology analysis. The sequence of these polynucleotides and oligonucleotides can be selected so as to avoid isolating nucleic acid encoding less homologous CoA-transferases by studying the amino acid sequence alignment plot provided in FIG. 2A, 2B, and 2C and targeting regions sharing little homology with the CoA-transferase from, for example, *Bacillus subtilis, Sus scrofa*, and *Caenorhabditis elegans*, FIG. 2A and 2B etc. The sequence of the polynucleotides and oligonucleotides to be used for isolating nucleotides encoding a polypeptide 80% homologous to Hp thiolase can be selected in a similar manner. Generally, probes encode regions of the Hp amino acid sequence of thiolase or CoA-transferase that share less the 75% identity with the other displayed sequences and such regions are at least 5 amino acids in length.

In another preferred aspect, the polynucleotide or oligonucleotide shares at least an 85% homology with the nucleic acid sequence encoding for Hp thiolase or CoA-transferase (SEQ ID NO.:04), in whole or in part. These polynucleotides most preferably include alleles of Hp thiolase or CoA-transferase, respectively, and can include thiolases or CoA-transferases isolated from other species of Helicobacter, such as, for example, *H. nemestrinae, H. acinonyx, H. heilmannii, H. felis, H. mustelae, H. rappini, H. muridarum, H. hepaticus, H. canis, H. fennelliae, H. cinaedi*, and other species that are later identified, preferably that inhabit a mammalian stomach, and most preferably species that can propagate in a low pH environment similar to that of the human stomach, namely pH 2–pH 4. Such species will tolerate a pH range of pH 2–pH 8, preferably pH 3–pH 5. Also included are polynucleotides located in tandem with CoA-transferase or thiolase and that encode other enzymes in the poly-3-hydroxybutyrate metabolic pathway, such as, for example, synthase. These polynucleotides can be isolated using polynucleotides and oligonucleotides derived from SEQ ID NO.:01 and SEQ ID NO.:16.

POLYPEPTIDES

In another embodiment, the invention provides polypeptides comprising (1) the full-length heterodimeric Hp CoA-transferase protein, (2) either Subunit A or Subunit B (SEQ ID NO.:02 and SEQ ID NO.:03) alone, (3) fragments of the amino acid sequence of SEQ ID NO.:02 or SEQ ID NO.:03, (4) a CoA-transferase protein, polypeptide, or polypeptide fragment having at least 80% amino acid homology as determined by BLAST homology analysis (with increasing preference for sequences with at least 85%, 90%, 95% to having an one amino acid difference) to an *Hp* CoA-transferase sequence, preferably identical to that of SEQ ID NOS.:02 and 03, (5) a full-length *Hp* thiolase protein, (6) the amino acid sequence of SEQ ID NO.:17 (Table 4), (7) fragments of the amino acid sequence of SEQ ID NO.:17, (8) a thiolase protein, polypeptide, or polypeptide fragment having at least 80% amino acid homology as determined by BLAST homology analysis (with increasing preference for sequences with at least 85%, 90%, 95% to having an one amino acid difference) to an *Hp* thiolase sequence, preferably identical to that of SEQ ID NO.:17, (9) any other enzyme in the *Hp* poly-3-hydroxybutyrate metabolic pathway that is encoded by a gene located in tandem with the genes encoding *Hp* CoA-transferase or thiolase. The polypeptides of the invention can include amino acids in addition to polypeptides or fragments homologous to *Hp* CoA-t or thiolase, provided that the polypeptides are less than 70% homologous to non-*Hp* CoA-t or thiolase amino acid sequences.

amino acids provided that the peptide fragment is less than 70% homologous to non-*Hp* CoA-transferase or thiolase amino acid sequences and at least 80% homologous to a portion of SEQ ID NO.:2, SEQ ID NO.:3 or SEQ ID NO.:17 corresponding to the amino acid sequence of the polypeptide fragment.

Analogs may also comprise amino acid substitutions, preferably conservative substitutions. Preferred amino acid substitutions are those which: (1) reduce susceptibility to proteolysis, (2) reduce susceptibility to oxidation, (3) alter binding affinity for CoA, and (4) confer or modify other physicochemical or functional properties of such analogs. Analogs can include various muteins of an *Hp* CoA-t or thiolase sequences other than the naturally-occurring peptide sequences. For example, single or multiple amino acid substitutions, provided that the analog retains a closer resemblance to Helicobacter CoA-t or thiolase than (i.e., that the analogs are less than 70% homologous to) the CoA-t or thiolase of other organisms.

A conservative amino acid substitution should generally not substantially change the structural characteristics of the

TABLE 4

Amino acid sequence of *H. pylori* thiolase polypeptide fragment

```
1   NSSGINDGAS IIILCSAKKA QKLGLKAMAT IRGFGLGGCS PDIMGICPSI  (SEQ ID NO.:17)
51  AIKNNLKNVK MNLNDINLFE LNEAFAAQSL AVLKELELNP NIVNVNGGAI
```

Fragments or analogs of *Hp* CoA-t or thiolase can be prepared by those of ordinary skill in the art. Preferred amino- and carboxy-termini of fragments or analogs occur near boundaries of functional domains. For example, functional domains of CoA-transferase include domains conferring the property of 3-oxoadipate-CoA-transferase, butyrate acetoacetate-CoA-transferase or preferably, 3-oxoacid-CoA-transferase enzymatic activity. Such domains can comprise the CoA acceptor or donor site, in whole or in part, or domains otherwise essential for CoA-t structure and/or function. Functional domains of thiolase include domains conferring the enzymatic properties of a 3-ketothiolase. Such domains can comprise the region of the polypeptide that can condense two molecules of acetyl CoA into acetoacetyl CoA or the region that can catalyze the reverse reaction or domains otherwise essential for thiolase structure and/or function. Preferably, computerized comparison methods are used to identify sequence motifs or predicted protein conformation domains that occur in other proteins of known structure and/or function. Methods to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in an *Hp* CoA-t sequence.

Although one class of preferred embodiments are fragments having amino- and/or carboxy-termini corresponding to amino acid positions near functional domains borders, alternative fragments may be prepared. The choice of the amino- and carboxy-termini of such fragments rests with the discretion of the practitioner and will be made based on experimental considerations, such as ease of construction, stability to proteolysis, thermal stability, immunological reactivity, amino- or carboxyl-terminal residue modification, or other considerations. Polypeptide fragments usually contain at least nine amino acids and can contain any number of parent sequence (e.g., a replacement amino acid should not tend to break a helix that occurs in the parent sequence, disrupt disulfide bonds or disrupt other types of secondary structure that characterizes the parent sequence). Examples of art-recognized polypeptide secondary and tertiary structures are described in *Proteins, Structures and Molecular Principles*, (1984) Creighton (ed.), W. H. Freeman and Company, New York; *Introduction to Protein Structure*, (1991), C. Branden and J. Tooze, Garland Publishing, New York, N.Y.; and Thornton et al. (1991) *Nature* 354: 105; which are incorporated herein by reference).

These isolated polypeptides provide reagents useful in drug discovery and can be used in in vitro assays, such as, for example, binding assays to identify potential drug candidates for the treatment of Helicobacter infection. In addition, these polypeptides can be used as antigens to raise antibodies that recognize a CoA-t or a thiolase, are preferably specific for a Helicobacter CoA-t or thiolase, and most preferably specific for an *Hp* CoA-t or thiolase. The polypeptides provided by the invention can also be used in the formulation of a vaccine for immunization against Helicobacter infection. Repetitive inoculations can be used to booster the immunization process.

In another aspect, the CoA-transferase or thiolase protein is naturally occurring and can be isolated from a cell extract by protein purification techniques known in the art, such as, for example, ion exchange column chromatography, high performance liquid chromatography (HPLC), reversed phase HPLC, or affinity chromatography using antibodies that recognize the CoA-t.

Alternatively, the isolated proteins and polypeptides are expressed using polynucleotides encoding the polypeptide (s) of the invention operably linked to an appropriate control sequence in an expression vector suitable for expression preferably in a bacterial cell, and also in mammalian, insect, or yeast cells, although eukaryotic cells are less preferred.

Usually, the *Hp* CoA-t or thiolase polynucleotide or a fragment thereof can be expressed in a bacterial system.

Such expression will usually depend on a bacterial promoter, which is any DNA sequence capable of binding bacterial RNA polymerase and initiating the downstream (3") transcription of a coding sequence (e.g. structural gene) into mRNA. Usually, a promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) (Raibaud et al. (1984) *Annu. Rev. Genet.* 18:173). Regulated expression can therefore be either positive or negative, thereby either enhancing or reducing transcription.

Sequences encoding metabolic pathway enzymes provide particularly useful promoter sequences. One such promoter sequence is the *Hp* CoA-t promoter, present in the first 72 nucleotides of SEQ ID NO.:1. This promoter is also recognized in *E. coli* and can lead to efficient transcription and translation of the *Hp* CoA-t gene. Other examples of useful promoters include promoter sequences derived from sugar metabolizing enzymes, such as galactose, lactose (lac) (Chang et al. (1977) *Nature* 198:1056), and maltose. Additional examples include promoter sequences derived from biosynthetic enzymes such as tryptophan (trp) (Goeddel et al. (1980) *Nuc. Acids Res.* 8:4057; Yelverton et al. (1981) *Nucl. Acids Res.* 9:731; U.S. Pat. No. 4,738,921; EPO Pub. Nos. 36,776 and 121,775). The β-lactamase (bla) promoter system, bacteriophage lambda PL (Shimatake et al. (1981) *Nature* 292:128) and T5 (U.S. Pat. No. 4,689,406) promoter systems also provide useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid promoter (U.S. Pat. No. 4,551, 433). For example, the tac promoter is a hybrid trp-lac promoter comprised of both trp promoter and lac operon sequences that is regulated by the lac repressor (Amann et al. (1983) *Gene* 25:167; de Boer et al. (1983) *Proc. Natl. Acad. Sci.* 80:21). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al. (1986) *J. Mol. Biol.* 189:113; Tabor et al. (1985) *Proc Nati. Acad. Sci.* 82:1074). In addition, a hybrid promoter can also be comprised of a bacteriophage promoter and an *E. coli* operator region (EPO Pub. No. 267,851).

In addition to a functioning promoter sequence, an efficient ribosome binding site is also useful for the expression of the *Hp* CoA-t or thiolase gene or fragment thereof in prokaryotes. In *E. coli*, the ribosome binding site is called the Shine-Dalgarno (SD) sequence and usually includes an initiation codon (ATG) and a sequence 3–9 nucleotides in length located 3–11 nucleotides upstream of the initiation codon (Shine et al. (1975) *Nature* 254:34). The SD sequence is thought to promote binding of mRNA to the ribosome by the pairing of bases between the SD sequence and the 3' end of *E. coli* 16S rRNA (Steitz et al. (1979) *In Biological Regulation and Development: Gene Expression* (ed. R. F. Goldberger)). To express eukaryotic genes and prokaryotic genes with weak ribosome-binding site, see Sambrook et al. (1989) "Expression of cloned genes in *Escherichia coli.*" *In Molecular Cloning: A Laboratory Manual*. In *Hp* CoA-t, the Shine Delgarno sequence includes nucleotides 62 to 65 of SEQ ID NO.:1.

*Hp* CoA-t, thiolase or other polypeptides of the invention can be expressed intracellularly. A promoter sequence can be directly linked with the *Hp* CoA-t or thiolase gene or a fragment thereof, in which case the first amino acid encoded at the N-terminus will be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase (EPO Pub. No. 219,237). A preferred expression construct is described in Example 6.

Fusion proteins provide an alternative to direct expression. Typically, a DNA sequence encoding the N-terminal portion of an endogenous bacterial protein, or other stable protein, is fused to the 5' end of a heterologous *Hp* CoA-t or thiolase coding sequence or other polypeptide of the invention. Upon expression, this construct will provide a fusion of the two amino acid sequences. For example, the bacteriophage lambda cell gene can be linked at the 5' terminus of the *Hp* CoA-t or thiolase gene or fragment thereof and expressed in bacteria. The resulting fusion protein preferably retains a site for a processing enzyme (for example, Factor Xa) to cleave the bacteriophage protein from the *Hp* CoA-t or thiolase gene product or fragment thereof (Nagai et al. (1984) *Nature* 309:810). Fusion proteins can also be made with sequences from the lacZ (Jia et al. (1987) *Gene* 60:197), trpE (Allen et al. (1987) *J. Biotechnol.* 5:93; Makoff et al. (1989) *J. Gen. Microbiol.* 135:11), and Chey (EPO Pub. No. 324,647) genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the *Hp* CoA-t or thiolase polypeptide. Through this method, mature *Hp* CoA-t polypeptides, thiolase polypeptides and other polypeptides of the invention can be isolated (Miller et al. (1989) *Bio/Technology* 7:698). Another preferred system is a fusion with glutathione-S-transferase ("GST"; available from Pharmacia) at the C-terminal end of *Hp* CoA-t, thiolase or a fragment thereof. The recombinant fusion protein is readily isolated by its ability to bind to glutathione attached to solid support followed by elution of the fusion with glutathione. Another preferred system is a fusion with a histidine tag at the N- or C-terminal end of *Hp* CoA-t, thiolase or a fragment thereof. The recombinant fusion protein is readily isolated by its ability to bind a $Ni^{2+}$-NTA resin.

Typically, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the above described components, comprising a promoter, signal sequence (if desired), coding sequence of interest, and transcription termination sequence, are operatively linked in an expression construct. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicon can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids. Either a high or low copy number vector can be selected, depending upon the effect of the vector and the *Hp* CoA-t or thiolase polypeptide on the host.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EPO Pub. No. 127, 328). Integrating vectors can also be comprised of bacteriophage or transposon sequences.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chloramphenicol, erythromycin, kanamycin (neomycin), and tetracycline (Davies et al. (1978) *Annu. Rev.Microbiol.* 32:469). Selectable markers can also include biosynthetic genes, such as those in the histidine, tryptophan, and leucine biosynthetic pathways. Alternatively, viral vectors can be used to express polypeptides of the invention.

Alternatively, some of the above described components can be put together in transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: *Bacillus subtilis* (Palva et al. (1982) *Proc. Natl. Acad. Sci. USA* 79:5582; EPO Pub. Nos. 36,259 and 63,953; PCT WO 84/04541), *Escherichia coli* (Shimatake et al. (1981) *Nature* 292:128; Amann et al. (1985) *Gene* 40:183; Studier et al. (1986) *J. Mol. Biol.* 189:113; EPO Pub. Nos. 36,776, 136,829 and 136,907; UK Patent Application Serial No. 8418273), *Streptococcus cremoris* (Powell et al. (1988) *Appl. Environ. Microbiol.* 54:655) *Streptococcus lividans* (Powell et al. (1988) *Appl. Environ. Microbiol.* 54:655), *Streptomyces lividans* (U.S. Pat. No. 4,745,056).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., (*Biotechniques* (1993) 14:225-226; Masson et al. (1989) *FEMS Microbiol. Lett.* 60:273; Palva et al. (1982) *Proc. Natl. Acad. Sci. USA* 79:5582; EPO Pub. Nos. 36,259 and 63,953; P.C.T. WO 84/04541, Bacillus), (Miller et al. (1988) *Proc. Natl. Acad. Sci.* 85:856; Wang et al. (1990) *J. Bacteriol.* 172:949, Campylobacter), (Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In Genetic Engineering: Proceedings of the International Symposium on Genetic Engineering (eds. H. W. Boyer and S. Nicosia); Mandel et al. (1970) *J. Mol. Biol.* 53:159; Taketo (1988) *Biochem. Biophys. Acta* 949:318; Escherichia), (Chassy et al. (1987) *FEMS Microbiol. Lett.* 44:173 Lactobacillus); (Fiedler et al. (1988) *Anal. Biochem* 170:38, Pseudomonas); (Augustin et al. (1990) *FEMS Microbiol. Lett.* 66:203, Staphylococcus), (Barany et al. (1980) *J. Bacteriol.* 144:698; Harlander (1987) "Transformation of *Streptococcus lactis* by electroporation," in: *Streptococcal Genetics* (ed. J. Ferretti and R. Curtiss III); Perry et al. (1981) *Infec. Immun.* 32:1295; Powell et al. (1988) *Appl. Environ. Microbiol.* 54:655; Somkuti et al. (1987) *Proc. 4th Evr. Cong. Biotechnology* 1:412, Streptococcus).

In another aspect, the polypeptide fragments can be synthesized chemically by techniques well known in the art, such as solid-phase peptide synthesis (Stewart et al., *Solid Phase Peptide Synthesis*, W. H. Freeman Co., San Francisco (1963)); Merrifield, *J Am Chem Soc* 85:2149–2154 (1963)). These and other methods of peptide synthesis are also exemplified by U.S. Pat. Nos. 3,862,925, 3,842,067, 3,972,859, and 4,105,602. The synthesis can use manual synthesis techniques or automatically employ, for example, an Applied BioSystems 430A or 431A Peptide Synthesizer (Foster City, Calif.) following the instructions provided in the instruction manual supplied by the manufacturer. It will be readily appreciated by those having ordinary skill in the art of peptide synthesis that the intermediates which are constructed during the course of synthesizing the present analog compounds are themselves novel and useful compounds and are thus within the scope of the invention.

In addition to polypeptides consisting only of naturally-occurring amino acids, peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) TINS p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity) but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 (—CH$_2$NH—, CH$_2$CH$_2$—); Spatola, A. F. et al., *Life Sci* (1986) 38:1243–1249 (—CH$_2$—S); Hann, M. M.,*J Chem Soc Perkin Trans I* (1982) 307–314 (—CH— CH—, cis and trans); Alnquist, R. G. et al., *J. Med Chem* (1980) 23:1392–1398 (—COCH$_2$—); Jennings-White, C. et al., *Tetrahedron Lett* (1982) 23:2533 (—COCH$_2$—); Szelke, M. et al., *European Appln.* EP 45665 (1982) CA: 97:39405 (1982) (—CH(OH)CH$_2$—); Holladay, M. W. et al., *Tetrahedron Lett* (1983) 24:4401–4404 (—C(OH)CH$_2$—); and Hruby, V. J., *Life Sci* (1982) 31:189–199 (—CH$_2$—S—); each of which is incorporated herein by reference. A particularly preferred non-peptide linkage is —CH$_2$NH—. Such peptide mirnetics may have significant advantages over polypeptide embodiments, including, for example: more economical production, greater chemical stability, enhanced pharmacological properties (half-life, absorption, potency, efficacy, etc.), altered specificity (e.g., a broad-spectrun of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with CoA (e.g., are not contact points in the CoA acceptor or donor sites). Derivitization (e.g., labelling) of peptidominetics should not substantially interfere with the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

DETECTION METHODS

In another embodiment, the invention provides methods for detecting the presence or absence of Helicobacter bacteria (or a bacteria that resides at low pH), preferably *Helicobacter pylori*, in a sample. These methods can be used by clinicians in diagnosing a propensity for or the pathology of various types of gastric disease, in particular gastritis, peptic ulcers and gastric cancer. For example, a biopsy of gastric fluid can be obtained from a patient and subjected to methods provided by the invention for the quantitative or qualitative detection of *Hp* CoA-transferase or thiolase genetic material or gene product. For some methods it is preferred to culture the gastric fluid in order to increase the population of bacteria to a detectable level and in some methods an additional culture step is unnecessary.

In a preferred aspect, the polynucleotides of the invention are used to detect the presence or absence of Helicobacter bacteria, preferably *Helicobacter pylori* bacteria. One method exploits the technique of high stringency hybridization. The sample can be prepared for hybridization by a number of procedures known in the art to result in bacterial cell lysis. Before or after cell lysis, the sample can be applied to a matrix, such as, for example, a nylon membrane. The genetic material in the sample can be applied to the matrix without extensive purification, as for a slot blot experiment (Example 4), or alternatively, the genetic material can be isolated, subjected to restriction endonuclease cleavage and gel electrophoresed prior to transfer to a matrix, as is commonly done in a Southern blot experiment (Example 1). The method of the invention is not limited to any particular procedures for preparing the genetic material or applying it to a matrix. Any procedure known in the art for the manipulation of genetic material can be used to practice the method of the invention. The matrix can be contacted with a probe comprising the polynucleotides or oligonucleotides of the invention under high stringency hybridization and washing conditions as described above.

Alternatively, the presence or absence of Helicobacter CoA-transferase or thiolase genetic material can be detected by subjecting a sample to amplification by polymerase chain reaction (PCR) using the polynucleotides or oligonucleotides of the invention and using a variety of procedures to detect an amplified Helicobacter CoA-t or thiolase polynucleotide fragment, such as, for example, gel electrophoresis (Examples 1, 2, and 3). Preferably, oligonucleotides are designed to comprise a sequence specific to a Helicobacter CoA-transferase or thiolase gene, most preferably a *Helicobacter pylori* CoA-transferase gene. Generally, the oligonucleotides comprise a sequence corresponding to a region within the sequence of SEQ ID NO.:01 or SEQ ID NO.:16 that shares at most an 85% homology with non-Helicobacter CoA-t or thiolase gene sequences, respectively.

In another preferred aspect, antibodies specific for Helicobacter obtained by immunizing animals with the polypeptides of the invention can be used to detect the presence or absence of Helicobacter CoA-transferase or thiolase protein in a sample and under some circumstances can be used to quantitate the level of infection by Helicobacter. Polypeptides used for the immunization of animals can be obtained by protein purification of naturally occurring Helicobacter CoA-t or thiolase, recombinant Helicobacter CoA-t or thiolase, or fragments thereof expressed in a host cell as described above. The isolated polypeptides of the invention can be used to immunize rabbits (See Example 5), mice, goats, chickens, or other animals known in the art to be amenable to such immunization. Monoclonal antibodies are preferred for the Helicobacter detection method of the invention and polyclonal antibodies can be used, provided that they do not cross-react with non-Helicobacter proteins. The method of the invention can employ immunoassays known in the art, such as, for example, ELISA, immunoprecipitation, radioimmunoassay, enzyme-linked-immunoassay, or western blot (See Example 7) experiments. Samples can be prepared according to the needs of the particular immunoassay to be used.

DRUG DISCOVERY

In another embodiment, the poly-3-hydroxybutyrate pathway, identified by the invention as being essential to *Helicobacter pylori* survival in a host, is a target for the development of drug candidates for the treatment of gastrointestinal diseases resulting from Helicobacter infection, such as, for example, gastritis and peptic ulcers. The polypeptides or polynucleotides of the invention, such as CoA-transferase, thiolase, and PHB synthase can be used in the identification of such drug candidates. In view of the critical role of CoA-transferase in the metabolic pathway of Helicobacter, inhibitors of CoA-transferase can be used to combat Helicobacter infection. As shown in Example 11, proper function of CoA-transferase is essential for Helicobacter survival. The polynucleotides of the invention can be expressed in random mutagenesis systems such as phage display or the yeast two-hybrid system for the identification of mutant peptide antagonists of CoA-transferase activity. Mutant peptides that bind to the immobilized or soluble CoA-t or CoA-t fragments of the invention can then be further characterized in a functional assay, such as, for example, inhibition of 3-oxoacid CoA-transferase activity (See Example 8) to identify antagonists of Helicobacter CoA-transferase.

In another embodiment, immobilized or soluble, CoA-t, CoA-t fragments, thiolase, thiolase fragments, or PHB synthase, purified or in an *Hp* or other cell lysate, can be used to screen combinatorial peptide and combinatorial chemical libraries and non-random recombinant and synthetic peptides and other compounds (such as non-peptide molecules) for binding and/or inhibition of the corresponding activity.

For instance, the *E. coli* reconstituted enzymatic assay described in Example 8 can be used to test a number of CoA-transferase substrate or transition state analogs to identify those having a selective effect on the Helicobacter but not on the mammalian CoA-transferase. Drug candidates can also be identified by assaying CoA-transferase inhibitory activity in an *Hp* lysate in a manner similar to that described in Example 8, but in the presence of an inhibitor of *Hp* thiolase. Inhibition of *Hp* thiolase results in a linear determination of CoA-transferase activity by allowing the accumulation of acetoacetyl CoA, an end product of CoA-transferase activity. One such inhibitor of *Hp* thiolase is iodoacetamide.

For example, one can test a number of succinate analogs classified according to the parameters varied. Type I analogs are those in which the distance separating the two carboxylic acid groups is varied. Some examples of Type I analogs include oxalate, malonate, glutarate and adipate. Type II analogs are those in which the substituents on the ethylene bridge between the carboxyl groups are varied. Some examples of Type II analogs include cis- and trans-cyclobutane-1,2-dicarboxylate, cis- and trans-cyclohexane-1,2-dicarboxylate, methylsuccinate, mercaptosuccinate, malate and aspartate, 2,2-difluorosuccinate and perffuorosuccinate (where hydrogen atoms in the ethylene bridge are replaced with fluorine). As shown in Example 11, methyl- and mercapto- succinate inhibit *Hp* CoA-transferase but not the mammalian homologue. Type III analogs are those in which the substituents on one of the two carboxyl groups are varied. Some examples of Type III analogs include monomethylsuccinate, succinamate, maleamate, N-ethylmaleamate, and 3-sulfopropanoate. Type IV analogs are those in which the orientation of the two carboxyl groups is varied. Some examples of Type IV analogs include maleic acid, trans diacid fumarate, and acetylenedicarboxylate. Still other analogs include succinomonohydroxamic acid as well as analogs to be identified during the screening process.

The effect of a compound on thiolase activity can be determined, for example, by measuring the accumulation in an *Hp* cell lysate of a CoA-transferase end product, acetoacetyl CoA in the presence and absence of such compound. The effect of a compound on PHB synthase activity can be determined, for example, by measuring the accumulation in an *Hp* cell lysate of polyhydroxyalkanoates (PHAs) in the presence or absence of such compound.

Also provided by the invention are inhibitors of CoA-transferase (such as, for example, methylsuccinate or mercaptosuccinate), inhibitors of thiolase, or inhibitors of PHB synthase identified by the drug discovery methods described above. Some compounds, identified by the methods of the invention to be inhibitors of the poly-3-hydroxybutyrate pathway, may have structures that have been previously known in the art. However, the use of such compounds as inhibitors of the PHB pathway is a novel feature of the present invention.

PHARMACEUTICAL COMPOSITIONS AND ADMINISTRATION

In another embodiment, pharmaceutical compositions containing the polynucleotides or oligonucleotides and polypeptides of the invention can be used as a therapeutic for the treatment of some gastrointestinal diseases caused by Helicobacter infection (or by bacteria that can reside at low pH) and treatable by abatement or eradication of Helicobacter infection. These compositions may be less effective in gastric diseases that have progressed beyond the stage of bacterial infections, such as gastric cancer although there are reports that gastric MALT lymphomas regress when *Hp* infection is cured. Preferably, the pharmaceutical compositions are designed for quick release in the low pH environment of the stomach. Absorption, tissue distribution and in vivo stability of antisense nucleotides following oral administration have been determined by those skilled in the art (Agrawal et al., *Biochemical Pharmacology* 50:571–576 (1995)).

In one aspect, an antisense polynucleotide corresponding to a sequence complementary to the sequence of SEQ ID NO.:01, SEQ ID NO.:16 or fragment thereof can be administered to a patient suffering from gastric disease. Delivery of normally negatively charged antisense oligonucleotides to the bacterial cell is expected to be facilitated by the low pH environment due to protonation of negative charges on the phosphates.

Antisense oligonucleotides of the invention may comprise any polymeric compound capable of specifically binding to a target polynucleotide by way of a regular pattern of monomer-to-nucleoside interactions, such as Watson-Crick type of base pairing, Hoogsteen or reverse Hoogsteen types of base pairing, or the like. Antisense compounds of the invention may also contain pendent groups or moieties, either as part of or separate from the basic repeat unit of the polymer, to enhance specificity, nuclease resistance, delivery, or other property related to efficacy, e.g. cholesterol moieties, duplex intercalators such as acridine, poly-L-lysine, "end capping" with one or more nuclease-resistant linkage groups such as phosphorothioate, and the like. Sequences of certain representative oligonucleotides useful in this invention are set forth in the Sequence Listing included herewith.

Antisense compounds of the invention include the pharmaceutically acceptable salts thereof, including those of alkaline earths, e.g. sodium or magnesium, ammonium or $NX_4^+$, wherein X is $C_1$–$C_4$ alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as $Na^+$, $NH_4^+$, or the like.

Preferably, nuclease resistance is conferred on the antisense compounds of the invention by providing nuclease-resistant internucleosidic linkages. Many such linkages are known in the art, e.g. phosphorothioate: Zon and Geiser, Anti-Cancer Drug Design, 6: 539–568 (1991); Stec et al, U.S. Pat. No. 5,151,510; Hirschbein, U.S. Pat. No. 5,166,387; Bergot, U.S. Pat. No. 5,183,885; phosphorodithioates: Marshall et al, Science, 259:1564–1570 (1993); Carathers and Nielsen, International application PCT/US89/02293; phosphoramidates, e.g. —OP(=O)(NR$^1$R$^2$)—O— with R$^1$ and R$^2$ hydrogen or $C_1$–$C_3$ alkyl: Jager et al, Biochemistry, 27:7237–7246 (1988); Froehler et al, International application PCT/US90/03138; peptide nucleic acids: Nielsen et al, Anti-cancer Drug Design, 8: 53–63 (1993), International application PCT/EP92/O1220; methylphosphonates: Miller et al, U.S. Pat. No. 4,507,433, Ts'o et al, U.S. Pat. No. 4,469,863, Miller et al, U.S. Pat. No. 4,757,055; and P-chiral linkages of various types, especially phosphorothioates, Stec et al, European patent application 92301950.9 and Lesnikowski, Bioorganic Chemistry, 21:127–155 (1993). Additional nuclease linkages include phosphoroselenoate, phosphorodiselenoate, phosphoroanilothioate, phosphoranilidate, alkylphosphotriester such as methyl- and ethylphosphotriester, carbonate such as carboxymethyl ester, carbamate, morpholino carbamate, 3'-thioformacetal, silyl such as dialkyl ($C_1$–$C_6$)- or diphenylsilyl, sulfamate ester, and the like. Such linkages and methods for introducing them into oligonucleotides are described in many references, e.g. reviewed generally by Peyman and Ulmann (cited above); Milligan et al (cited above); Matteucci et al, International application PCT/US91/06855. Preferably, phosphorus analogs of the phosphodiester linkage are employed in the compounds of the invention, such as phosphorothioate, phosphorodithioate, phosphoramidate, or methylphosphonate. More preferably, phosphorothioate is employed as the nuclease resistant linkage. It is understood that in addition to the preferred linkage groups, compounds of the invention may comprise additional modifications, e.g. boronated bases, Spielvogel et al, U.S. Pat. No. 5,130,302; cholesterol moieties, Shea et al, Nucleic Acids Research, 18:3777–3783 (1990) or Letsinger et al, Proc. Natl. Acad. Sci., 86:6553–6556 (1989); 5-propenyl modification of pyrimidines, Froehler et al, Tetrahedron Lett., 33: 5307–5310 (1992); and the like.

Preferably, antisense compounds of the invention are synthesized by conventional means on commercially available automated DNA synthesizers, e.g. an Applied Biosystems (Foster City, Calif.) model 380B, 392 or 394 DNA/RNA synthesizer. Preferably, phosphoramidite chemistry is employed, e.g. as disclosed in the following references: Beaucage and Iyer, Tetrahedron, 48:2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like.

In embodiments where triplex formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "–" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88:9397–9401 (1991); Roberts et al, Science, 258:1463–1466 (1992); Distefano et al, Proc. Natl. Acad. Sci., 90:1179–1183 (1993); Mergny et al, Biochemistry, A 30:9791–9798 (1991); Cheng et al, I. Am. Chem. Soc., 114:4465–4474 (1992); Beal and Dervan, Nucleic Acids Research, 20:2773–2776 (1992); Beal and Dervan, 1. Am. Chem. Soc., 114:4976–4982 (1992); Giovannangeli et al, Proc. Natl. Acad. Sci., 89: 8631–8635 (1992); Moser and Dervan, Science, 238:645–650 (1987); McShan et al, J. Biol. Chem., 267:5712–5721 (1992); Yoon et al, Proc. Natl. Acad. Sci., 89:3840–3844 (1992); Blume et al, Nucleic Acids Research, 20:1777–1784 (1992); and the like.

The length of the oligonucleotide moieties is sufficiently large to ensure that specific binding will take place only at the desired target polynucleotide and not at other fortuitous sites, as explained in many references, e.g. Rosenberg et al, International application PCT/US92/05305; or Szostak et al, Meth. Enzymol. 68:419–429 (1979). The upper range of the length is determined by several factors, including the inconvenience and expense of synthesizing and purifying oligomers greater than about 30–40 nucleotides in length, the greater tolerance of longer oligonucleotides for mismatches than shorter oligonucleotides, whether modifications to enhance binding or specificity are present, whether duplex or triplex binding is desired, and the like. Usually, antisense compounds of the invention have lengths in the range of about 12 to 60 nucleotides. More preferably, antisense compounds of the invention have lengths in the range of about 15 to 40 nucleotides; and most preferably, they have lengths in the range of about 18 to 30 nucleotides.

The antisense oligonucleotides of the invention can be synthesized by any of the known chemical oligonucleotide synthesis methods. Such methods are generally described, for example, in Winnacker, *From Genes to Clones: Introduction to Gene Technology*. VCH Verlagsgesellschaft mbH (H., Ibelgaufts trans. 1987). Any of the known methods of oligonucleotide synthesis can be utilized in preparing the instant antisense oligonucleotides. The antisense oligonucleotides are most advantageously prepared by utilizing any of the commercially available, automated nucleic acid synthesizers. The device utilized to prepare the oligonucleotides described herein, the Applied Biosystems 380B DNA Synthesizer, utilizes β-cyanoethyl phosphoramidite chemistry.

Oligonucleotides complementary to and hybridizable with any portion of the *Hp* CoA-t or thiolase mRNA transcript are, in principle, effective for inhibiting translation of the transcript, and capable of inducing the effects herein described. Translation is most effectively inhibited by blocking the mRNA at a site at or near the initiation codon. Thus, oligonucleotides complementary to the 5'-terminal region of the *Hp* CoA-t or thiolase mRNA transcript are preferred. Secondary or tertiary structure which might interfere with hybridization is minimal in this region. The antisense oligonucleotide is preferably directed to a site at or near the ATG initiation codon for protein synthesis. Oligonucleotides complementary to a portion of the Hp CoA-t or thiolase mRNA including the initiation codon are preferred. While antisense oligomers complementary to the 5'-terminal region of the Hp CoA-t or thiolase transcript are preferred, particularly the region including the initiation codon, it should be appreciated that useful antisense oligomers are not limited to those complementary to the sequences found in the translated portion of the mRNA transcript, but also includes oligomers complementary to nucleotide sequences contained in, or extending into, the 5'- and 3'-untranslated regions.

Preferably, the thermal stability of the antisense oligonucleotides of the invention are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and antisense oligonucleotide concentrations at between about 1.0–2.0 $\mu$M. Typical conditions are as follows: 150 mM NaCl and 10 mM $MgCl_2$ in a 10 mM sodium phosphate buffer (pH 7.0) or in a 10 mM Tris-HCl buffer (pH 7.0); or like conditions. Data for melting curves are accumulated by heating a sample of the antisense oligonucleotide/target polynucleotide complex from room temperature to about 85–90° C. As the temperature of the sample increases, absorbance of 260 nm light is monitored at 1° C. intervals, e.g. using a Cary (Australia) model 1E or a Hewlett-Packard (Palo Alto, Calif.) model HP 8459 UV/VIS spectrophotometer and model HP 89100A temperature controller, or like instruments. Such techniques provide a convenient means for measuring and comparing the binding strengths of antisense oligonucleotides of different lengths and compositions.

In another aspect, the polypeptides of the invention that comprise a domain essential for CoA-transferase or thiolase activity that have the desired characteristics for bioavailabllity, stability and other important parameters of pharmacokinetics in vivo can be used as a competitive inhibitor of CoA-transferase or thiolase activity. Appropriate polypeptides can include fragments having an amino acid sequence corresponding to a partial sequence of SEQ ID NO.:02, SEQ ID NO.:03, SEQ ID NO.:17 or analogs or peptidomimetics of Helicobacter CoA-t.

In yet another aspect, a pharmaceutical composition comprises a compound that inhibits the activity of CoA-transferase, thiolase or PHB synthase. Such compound can be identified by any of the methods described above in the "Drug Discovery" section.

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. For example, in water soluble formulations the pharmaceutical composition preferably includes a buffer such as a phosphate buffer, or other organic acid salt, preferably at a pH of between about 7 and 8. For formulations containing weakly soluble antisense compounds, microemulsions may be employed, for example by using a nonionic surfactant such as Tween 80 in an amount of 0.04–0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g. Remington's Pharmaceutical Science, latest edition (Mack Publishing Company, Easton, Pa.).

An effective amount of CoA-transferase or thiolase oligonucleotide for particular applications depends on several factors, including the chemical nature of the antisense oligonucleotide, the disorder being treated, the method of administration, and the like. Preferably, an effective amount will provide a concentration of CoA-transferase or thiolase antisense oligonucleotide of between about 1 to 100 $\mu$M at the target polynucleotide; and more preferably, an effective amount will provide a concentration of antisense oligonucleotide of between about 1 to 10 $\mu$M at the target polynucleotide.

Depending on the structural and stability characteristics of a compound identified as an inhibitor of the PHB pathway, the per unit dosage and precise formulation of the pharmaceutical composition may vary. Typically, such compound would be administered orally at a dose ranging from 0.08 mg to 5 g daily, preferably between 0.2 mg to 0.2 g daily, most preferably between 0.8 mg to 100 mg daily. Preferably the compound would be administered multiple times per day and can be administered in a single dose, although this is less preferred. Typically, the drug delivery vehicle, whether liquid, gel, tablet, or another vehicle, will permit effective release of the compound at the site of infection. The drug delivery vehicle can provide for either immediate release or systematic release over time at the site of infection. The inhibitor compound can be administered parenteraly, such as intravenously, but this is less preferred. The compound can also be administered prophylactically to prevent the onset of gastric disease associated with Helicobacter infection.

The tablets, troches, pills, capsules and the like may also contain the following: a binder such as polyvinylpyrrolidone, gum tragacanth, acacia, sucrose, corn starch or gelatin; an excipient such as calcium phosphate, sodium citrate and calcium carbonate; a disintegrating agent such as corn starch, potato starch, tapioca starch, certain complex silicates, alginic acid and the like; a lubricant such as sodium lauryl sulfate, talc and magnesium stearate; a sweetening agent such as sucrose, lactose or saccharin; or a flavoring agent such as peppermint, oil of wintergreen or cherry flavoring. Solid compositions of a similar type are also employed as fillers in soft and hard-filled gelatin capsules; preferred materials in this connection also include lactose or milk sugar as well as high molecular weight polyethylene glycols. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, flavoring such as cherry or orange flavor, emulsifying agents and/or suspending agents, as well as such diluents as water, ethanol, propylene glycol, glycerin and various like combinations thereof. Of course, any material used in preparing any dosage unit form should be pharmaceutically pure and substantially non-toxic in the amounts employed.

EXAMPLES

Example 1

Cloning *Helicobacter pylori* (*Hp*) CoA-Transferase Amplification of *Hp* DNA by the polymerase chain reaction and screening of *Hp* lambda ZAP II library The CoA-transferase was originally found in *Helicobacter pylori* unexpectedly by using primers designed for the cloning of genes encoding P-ATPase-like proteins. *Hp* 69A chromosomal DNA was prepared according to the method described by Hua et al., *Helicobacter pylori: techniques for clinical diagnosis & basic research*, Chap. 9, pp121–127, Eds A. Lee & F. Megraud, WB Sauders Company LTD (1996) and randomly amplified by polymerase chain reaction (PCR) using primers having the sequence of SEQ ID NO.:04 and SEQ ID NO.:05 (ICT 14 and ICT 20). Strain 69A (Department of Medical Microbiology, Amsterdam University, The Netherlands) was isolated from a patient with non-ulcer dyspepsia. Optimal PCR conditions were established using the PCR optimization kit (Boehringer Mannheim). PCR was carried out in 50 µl containing 500 ng of *Hp* genomic DNA, 50 pmoles of each primer, 200 µM each of dNTP (Boehringer Mannheim) and a 28:1 mixture of TaqStart antibody (Clontech)+TaqDNA polymerase (Boehringer Mannheimn) final concentration 56 and 2 pM, respectively, in 10 mM TRIS-HCl, pH 9.2, 50 mM KCl and 1.5 mM $MgCl_2$. The cycling program was: 1 cycle of 94° C., 3 min.; 50° C., 2 min.; 72° C., 3 min. followed by 35 cycles of 94° C., 30 sec.; 50° C., 30 sec.; 72° C.; 1 min. and 1 cycle of 94° C., 20 sec.; 50° C., 20 sec.; 72° C., 5 min. in a microprocessor controlled incubation system, Crocodile III, Appligene. The resultant PCR product of approximately 1 Kb was partially sequenced and found to encompass $A^1TGAA-AACCG^{984}$ of SEQ ID NO.:1. Sequence analysis revealed a striking homology with part of the genes encoding the two subunits of the CoA-transferase family, a class of enzyme involved in energy metabolism.

To verify the specificity of the PCR fragment as a probe, Helicobacter chromosomal DNA from strain 69A and NCTC 11637 (kindly provided by Dr. A. Labigne, Pasteur Institute, Paris, France) were cleaved with the restriction enzyme HaeIII and hybridized with the PCR fragment.

SOUTHERN BLOTTING

HaeIII digestions of 10 µg of bacterial genomic DNA were run in 0.7% agarose gels in 0.5× TBE buffer and transferred to nylon membranes (Boehringer Mannheim) using a semi-dry electrophoresis transfer cell (Trans-Blot® SD, Bio-Rad) according to manufacturers' instructions (Bio-Rad). After denaturation, DNA was crosslinked to the membranes. Membranes were prehybridized at least 30 min. in DIG Easy Hyb solution (Boehringer Mannheim). After addition of the labeled probe and overnight hybridization at 21° C. or at 37° C. in DIG Easy Hybridization Solution (Boehringer), membranes were washed at different stringency conditions (twice in 2× SSC, 0.1% SDS for 5 min. at 21° C. and twice in 0.1× SSC, 0.1% SDS for 15 min. at the indicated temperature) with constant agitation. Blocking of the membrane background and ECL detection were performed according to manufacturers' instructions (ECL detection system, version II; Amersham). Exposure times of all membranes to X-ray films (X-Omat™ AR, Kodak) were chosen to visually optimize the chemiluminescent signals. A strong positive signal was observed with both strain DNAs (FIG. 3).

The above-mentioned PCR fragment was then used as a probe for the screening of a *Helicobacter pylori* chromosomal Zap II library. The lambda ZAP® II custom *Hp* genomic library (Stratagene) was titered and screened according to Stratagene supplier protocols except that probes were labeled with fluorescein-dUTP using a random prime labelling system (Amersham). Phages were amplified in *E. coli* XL-1 Blue cells (Stratagene). *E. coli* strains were grown in Luria-Bertani (LB) medium at 30 or 37° C. Solid media was prepared by addition of 1.5% bacto-agar (Difco). The antibiotics used were: 50 ug/ml ampicillin, 12.5 ug/ml tetracyclin and 40 ug/ml kanamycin (Sigma). Phages were then transferred to nylon membranes and hybridized with the labeled probe as described above. Fourteen positive clones were isolated from the screening of $10^6$ phages and the corresponding pbluescript SK plasmids excised from the lambda ZAP II using the ExAssist/SORL system according to the manufacturers' instructions (Stratagene). After automatic excision, five plasmids (named pGB1 to 5) were identified. Sequencing of pGB1 led to the identification of a ~2000 base pairs fragment of *Hp* genomic DNA containing a specific sequence of 1395 nucleotides in length, which encodes *Helicobacter pylori* CoA-transferase and portions of its associated 3' and 5' non-coding regions.

Example 2

Alternative Methods for Cloning *Hp* CoA-Transferases

The coding region for the entire *Hp* CoA-transferase gene is cloned or sub-cloned, as was done for the purpose of raising antibodies reactive with subunit A or subunit B (Example 5), by amplifying *Hp* 69A chromosomal DNA by PCR using primers having the sequence of SEQ ID NO.:06 and SEQ ID NO.:07 using conditions described in Example 1.

The coding region for Subunit A of *Hp* CoA-transferase is cloned in a similar manner using primers having the sequence of SEQ ID NO.:06 and SEQ ID NO.:08.

The coding region for Subunit B of *Hp* CoA-transferase is cloned in a similar manner using primers having the sequence of SEQ ID NO.:09 and SEQ ID NO.:07.

Example 3

Detention of *Hp* CoA-transferase Genes in Bacterial Samples

Figure 4:
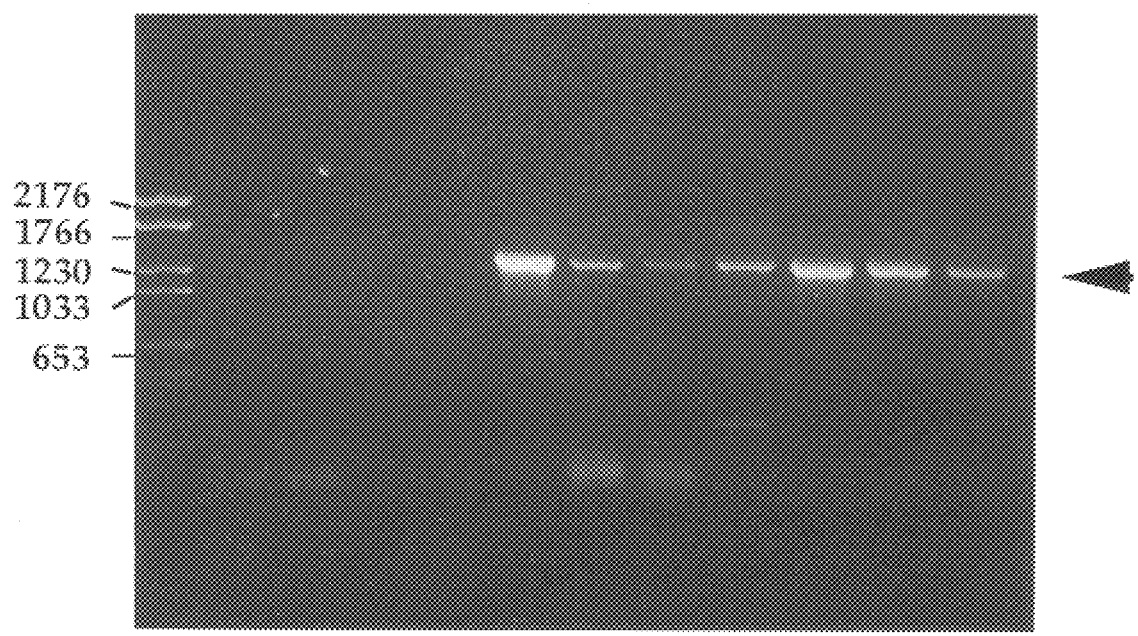
FIG. 4 shows strained PCR products in any electrophoresis agarose gel. The Hp CoA-t AB subunits were amplified using genomic DNA as template and the ICT45 and ICT48 oligonucleotides as primers to yield a polynucleotide fragment encompassing $A^{73}TGAA$ to $ATAGC^{1395}$ of SEQ ID NO:1. Lane 1: molecular weight standard VI, Boehringer Mannheim. Sizes in base pairs are indicated next to the panel; lane 2: control (no DNA); lane 3: *E. coli* JM 105; lane 4: *C. jejuni*; lane 5: *H. felis*; lane 6: Hp 69A; lane 7: Hp NCTC 11637; lane 8: Hp 880-0; lane 9: Hp ATCC 43504; lane 10: Hp Ly2; lane 11: Hp Ly4 and lane 12: Hp Lyl3.

The ubiquity of the putative CoA-transferase gene(s) in different Helicobacter strains was then monitored by PCR on chromosomal DNA by amplifying the 1322 base pairs fragment corresponding to the whole operon (FIG. 4). Chromosomal DNA was isolated from *E. coli* JM 105 (Pharmacia), *Campylobacter jejuni* (*Cp*) (Institute of Microbiology, CHUV, Lausanne), *Helicobacter felis* (*Hf*) (ATCC 49179), *Hp* 69A, *Hp*17 NCTC 11637, *Hp* 880-0 (Department of Medical Microbiology and Immunology, Hamburg University, Germany: isolated from a patient with a duodenal ulcer, strain NCTC 11637), *Hp* ATCC 43504, *Hp* Ly-2, *Hp* Ly-4, *Hp* LY-13 (Division of Gastroenterology, CHUV Lausanne: isolated from patient suffering from gastric cancer).

*Hp* strains were grown on agar plates made of 3.7% brain-heart infusion (BioMerieux) containing 0.25% yeast extract (Difco) supplemented with 10% sheep blood and maintained in a microaerophilic atmosphere (85% $N_2$/10% $CO_2$/5% $O_2$) at 37° C. for 2–3 days at pH 7.0. Brain-heart infusion, a growth supplement composed of 200 g/l veal brain infusion, 250 g/l beef heart infusion, 10 g/l gelatin, 5 g/l sodium chloride, 2.5 g/l disodium phosphate, and 2 g/l glucose, is prepared fresh for same day use by dissolving 37 g in one liter distilled water and autoclaving at 120° for 15–20 minutes. Solid media contained 3.6% GC agar base (Gibco) supplemented with 1% Isovitale X (Baltimore Biological Laboratories) and 10% donor horse serum (Biological Industries, Kibbutz Beth Haemek, Israel). Bacteria were harvested in BHI. The concentration of bacteria was determined by measuring optical density (OD) at 660 mm, where one OD unit corresponded to $10^8$ bacteria. Broth cultures were inoculated at an OD 0.05–0.1 using the same medium, with identical supplements, except that 10% foetal calf serum (Biological Industries, Kibbutz Beth Haemek, Israel), was used instead of sheep blood. The bacteria were grown in a microaerophilic atmosphere (5% $O_2$, 10% $CO_2$, 85% $N_2$) at 37° C. with gentle shaking for 24 to 36 hours. Cp and Hf were cultivated in blood-agar plates and maintained in the same conditions.

The Hp CoA-T AB subunits were amplified as described in Example 1 using 500 ng genomic DNA from each individual sample as template and primers having the sequence of SEQ ID NO.:10 and SEQ ID NO.:11 to yield a 1322 base pairs product, which was then subjected to agarose gel electrophoresis and stained with 0.5 µg/ml of ethidium bromide.

All Hp strains tested (Lanes 6–12) presented a positive signal. In contrast, no specific band was observed when using genomic DNA of E. coli JM 105, C. jejuni, or H. felis.

Example 4

Figure 5:
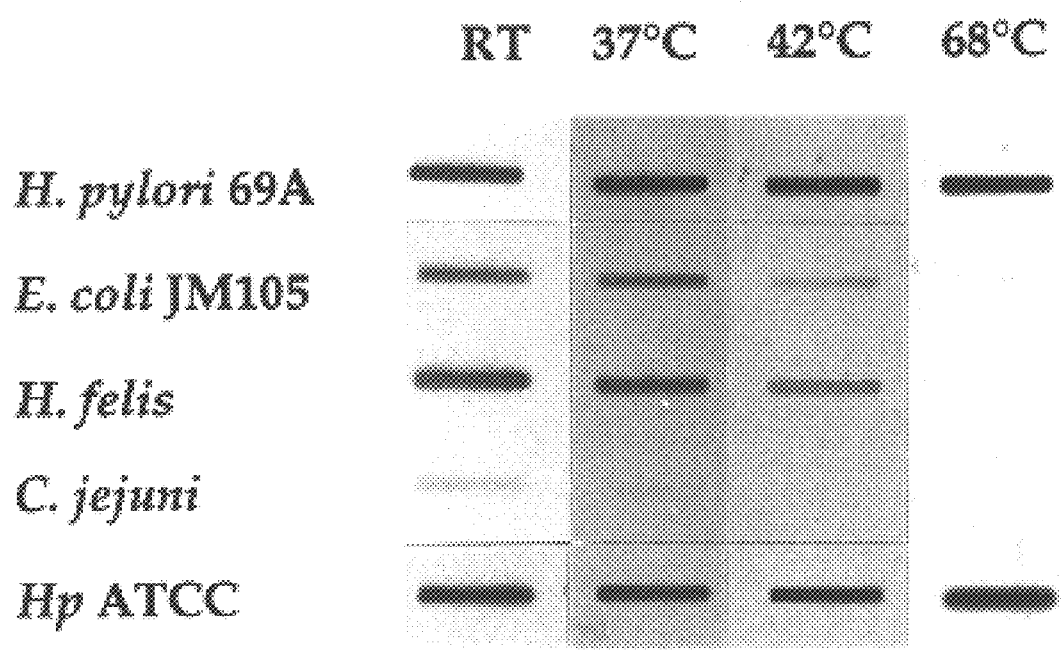
FIG. 5 shows a slot blot of different bacterial genomic DNA. Genomic DNAs (2 μg) were slot blotted. Membranes were prehybridized at room temperature (RT) for 1 hour and hybridized overnight with the labeled Hp CoA-t AB probe at the same temperature. Washes were performed twice in 2× SSC, 0.1% SDS for 5 minutes at RT and twice in 0.1× SSC, 0.1% SDS for 15 minutes at the indicated temperatures.

Alternative Method for Detection of Hp Co-A Tranderase Polynucleotides in a Sample To confirm the presence or absence of Hp CoA-T similar sequences in bacteria, bacterial DNA from Hp 69A, E. coli JM 105, C. jejuni, H. Felis, and Hp strain ATCC 43504 was analyzed by slot blotting and hybridization using different stringency conditions (FIG. 5). Prior to application to the nitrocellulose membranes (Bio-Rad), 2 µg of genomic DNA samples were denatured by addition of NaOH and EDTA solution to final concentrations of 0.4 M and 10 mM, respectively; heated at 100° C. for 10 minutes and neutralized by adding an equal volume of cold 2 M ammonium acetate pH 7.0. Treatment of the membranes and vacuum filtration of denatured DNA samples were performed according to the manufacturers' instructions (Bio-Dot® SF Microfiltration, Bio-Rad). After filtration, DNA was crosslinked to the membranes (UV Crosslinker; Hoefer Scientific Instruments). Membranes were prehybridized at room temperature for one hour and hybridized overnight with the labeled Hp CoA-t AB probe nt 73-1394, which encompasses $A^{73}$ TGAA to $TATAG^{1394}$ of SEQ ID NO.:1, at the same temperature in DIG Easy Hybridization Solution (Boehringer). Washes were performed twice in 2x SSC, 0.1% SDS for 5 min. at RT and twice in 0.1x SSC, 0.1% SDS for 15 min. at the indicated temperature. At the highest stringency wash conditions used (68° C.) only the DNA from Hp strains were detected. DNA from E. coli JM 105 was hardly visible when washes were performed at 42° C. indicating that the homology between the E. coli and the Hp protein was below 55%.

Example 5

Preparation of Antibodies Against Hp CoA-teandferase Protein

Figure 6A:
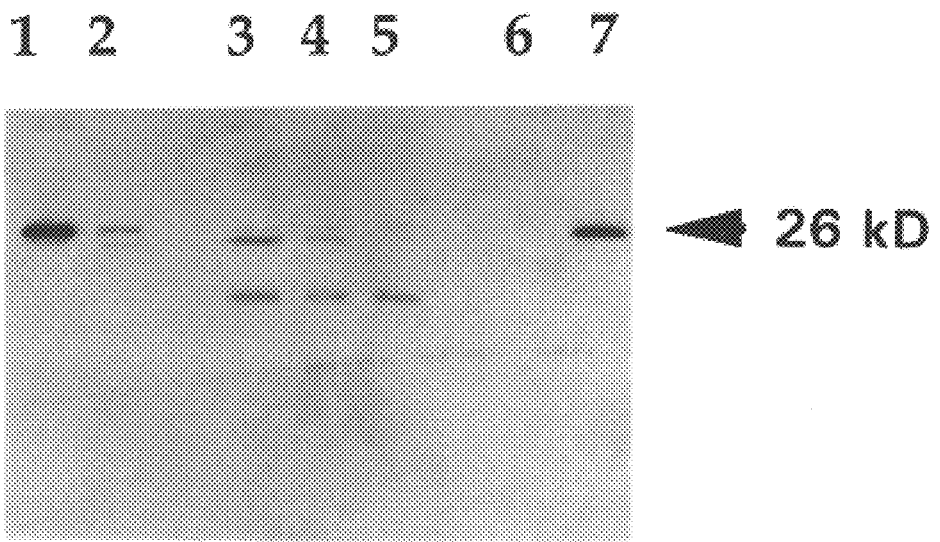
FIGS. 6A and 6B show Western blots of Hp CoA-t A and B subunits from Hp 69A, expressed in *E. coli* and detected with IgG Hp CoA-t A antibody (FIG. 16.6A) and Hp CoA-t B antibody (FIG. 6B); lane 1: whole cell lysate of *E. coli* JM105 producing Hp CoA-t A subunit coupled to a histidine tag (pDB4); lane 2: whole cell lysate of *E. coli* JM105 producing Hp CoA-t B subunit coupled to a histidine tag (pDB5); lanes 3 to 5, whole cell lysates of Hp grown on plate without, with 1 mM and 5 mM acetoacetate, respectively; lane 6: whole cell lysates of *E. coli* JM105 transformed with pUreA; lane 7 transformed with pCoA-t. Arrows indicate the positions of A (26 kD) and B (24 kD) subunits. Lanes 1, 2, 6 and 7 contain 1 μg total protein, lanes 3 to 5, 10 μg, which were run on a reducing 15% polyacrylamide gel+0.1% SDS.
Figure 6B:
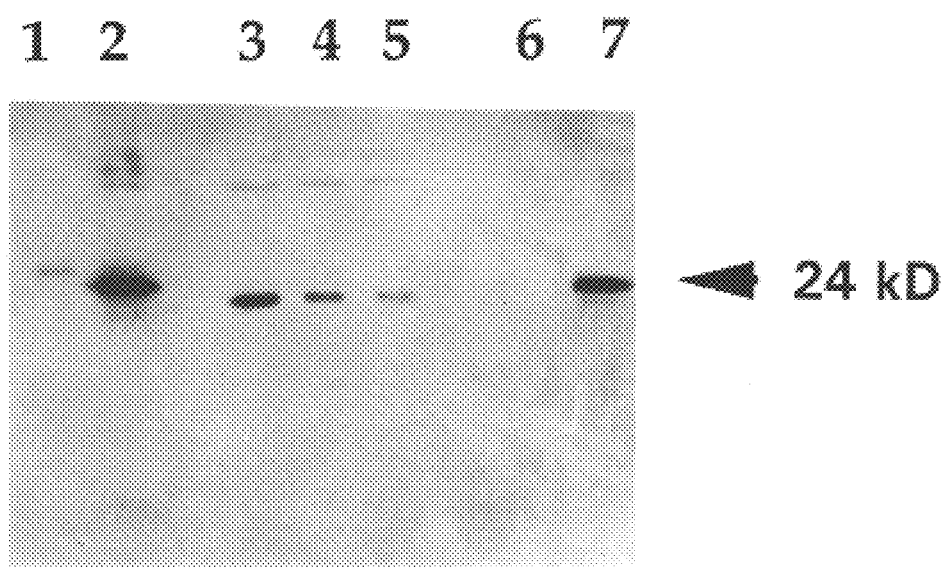

The coding regions for Subunit A and Subunit B of Hp CoA-transferase were cloned separately into pQE11 (pDB4 and pDB5) and overexpressed separately in E. coli M15 with an N-terminal histidine tag. The histidine tag is a stretch of 6 histidine that permits purification of tagged proteins to greater than 95% homogeneity in just one step (Janknecht et al., Proc. Natl. Acad. Sci. USA 88:8972–8976 (1991)). The histidine tagged-fusion proteins were isolated from inclusion bodies and purified under denaturing conditions by affinity chromatography on $Ni^{2+}$-NTA resin as described in the manufacturer's protocols (Diagen). The predicted size of each subunit is 26 kDa for Subunit-A and 24 KDa for Subunit-B, based on the amino acid sequence and the additional amino acids Met-Arg-Gly-Cys-His-His-His-His-His-His-Gly-Ser-Arg provided by the construct (4 amino acids in the parental vector+6 histidines in the tag+3 amino acids from the multiple cloning site). The purified products were provided to an antibody production company (Eurogentec) and used to obtain specific rabbit IgGs recognizing the Hp CoA-transferase A subunit or B subunit, respectively. The anti-Subunit-A and the anti-Subunit-B antibodies were then used to detect the endogenous Hp CoA-transferase or the protein made in E. coli. Lysates were electrophoresed by reducing SDS PAGE and a western blot was prepared according to the method provided in Example 7 using the anti-Subunit-A and anti-Subunit-B antibodies. As shown in FIGS. 6A and 6B, the anti-Subunit-A antibody recognizes the A subunit in lane 1 but nothing in lane 2. The anti-Subunit-B antibody recognizes the B subunit in lane 2 but nothing in lane 1. Thus, each antibody recognized a separate protein of 26 kDa (Subunit-A) or 24 kDa (Subunit-B) in Hp and E. coli extracts, confirming the specificity of the antibodies for each subunit.

Example 6

Recombinant Expression of Hp CoA-transferase Protein in a Host Cell

The entire coding region ($A^{73}$TGAA-$TATAG^{1394}$ of SEQ ID NO.:1) of Hp CoA-transferase was inserted into pKK223-3, a vector providing an IPTG-induced expression system using the tac promoter using EcoRI and PstI (resulting in plasmid pCoAT) and overexpressed in E. coli JM 105. Cells were grown overnight at 37° C. in 25 ml LB/50 µg/ml ampicillin, transferred to a 200 ml culture and grown up to A600≈0.25. Cells were stimulated with 100 µM isopropyl-β-D-thiogalactopyranoside (IPTG, Stratagene) for 1 hr and harvested by centrifugation at 3,000xg for 10 min. Hp 69A was grown on plate with or without 1 mM acetoacetate.

Lysates were electrophoresed according to the method provided in Example 5. If the CoA-t enzyme would originate from a monomeric enzyme and be cleaved proteolytically as it is the case for the pig enzyme, the two antibodies would recognize a monomeric precursor of 50–60 kDa. If it is not the case, the two antibodies would recognize two separate bands of different molecular weights. Two distinct bands corresponding to proteins of approximately 26 kDA and 24 kDa were detected by Western blotting with specific antibodies directed against the Subunit A and Subunit B, but no bands corresponding to proteins 50–60 kDa in size were detected (even when the protease inhibitor, PMSF, was included), confirming the fact that the Hp CoA-t operon encodes two separate subunits as predicted from sequence analysis (FIGS. 6A and 6B, lane 7). The antibodies do not recognize any non specific proteins in E. coli extracts transformed with a construct encoding an irrelevant protein such as the Helicobacter urease A subunit (FIGS. 6A and 6B, lane 6).

Example 7

Detection of Hp CoA-transferase Protein in a Sample

For detection of Hp gene products in Helicobacter or transformed E. coli, bacterial pellets of cultures grown in the absence or presence of 1 or 5 mM acetoacetate using the conditions provided in Example 3 were resuspended in activity buffer (see below) and sonicated (FIGS. 6A and 6B, lanes 3 to 5). Samples originating from gastric fluid are cultured under the conditions in order to increase the density of the population to a detectable level. Sonicates were run on 12% SDS-PAGE gels and transferred onto nitrocellulose membranes by electroblotting. After blocking in 5% powdered milk, filters were incubated overnight with rabbit IgGs directed against Hp Subunit A or Hp Subunit B, and washed four times in Tris-saline buffer pH 7.4, including two washes supplemented with 0.05% NP40. Filters were then incubated for 60 minutes with goat anti-rabbit IgG antibodies coupled to horseradish peroxidase. For development, chemiluminescence detection was used (ECL, Amersham Laboratories, Amersham, England), according to the supplier's directions. Helicobacter samples and samples from E. coli transformed with Hp CoA-transferase Subunit A or Subunit B, but not samples from E. coli transformed with urease, contained Hp CoA-transferase that could be detected with the mentioned antibodies.

Example 8

Measurement of Recombinant 3-oxoacid-CoA-transferase Acativity in Bacterial Sample Preparation of Bacterial Lysates For 3-oxoadipate-CoA and 3-oxoacid CoA-transferase assays (FIGS. 7A, 7B, and 7C), E. coli cells transformed with pCoAT, which contains $A^{73}$TGAA-TATAG$^{1394}$ of SEQ ID NO.:1 or with pUrea a plasmid containing the gene for urease (Labigne et al., J. Bacteriol. 173:1920–1931 (1991)) as a negative control, were washed once with M9 salts minimal medium (Molecular Cloning, a laboratory manual, Sambrook, Fritsch and Maniatis, second edition), pellets were stored at −20° C. until just prior to disruption. Thawed cell pellets were resuspended in 1 ml 50 mM phosphate buffer (pH 6.8), 1 mM dithiothreitol (Merck). Cell suspensions were disrupted by sonication and cellular debris removed by centrifugation. For butyrate-acetoacetate-CoA-transferase assays, the buffer used for cell wash and pellets resuspension was: 50 mM MOPS (pH 7.0), 0.5 M (NH4)$_2$SO4, 20% (v/v) glycerol, 1 mM EDTA. Protein concentration in cellular extracts was determined by Bradford's method (1976) using γ globulin as standard (Bio-Rad) and activity expressed in U/mg of protein.

3-Oxoadipate-CoA-Transferase Activity Assay

The 3-oxoadipate-CoA-transferase assay was performed as previously described (Yeh and Ornston, 1981). Briefly, the assay mix contained 10 mM β-ketoadipate (Sigma), 400 μM succinyl-CoA (Fluka) and 40 mM MgCl2 in 200 mM Tris-HCl buffer, pH 8.0. After addition of cell extract, the increase in $A_{305}$ (corresponding to the formation of the β-ketoadipyl-CoA-Mg$^{2+}$ complex) was measured every minute during 4 min. One unit of enzyme activity is defined as the amount of enzyme required to convert 1 μmol of substrate to product in 1 min under the assay conditions used (0.25 increment at 305 nm implies formation of 0.01 μmol of β-ketoadipyl-CoA-Mg$^{2+}$ complex).

Recombinant Butyrate-Acetoacetate-CoA-Transferase Activity Assay

Activity was measured by monitoring the decrease in A310 due to the disappearance of acetoacetyl-CoA, as previously described (Cary et al., 1990; Weisenborn et al., 1989). The assay was performed in a 100 mM Tris-HCl pH 7.5 containing 5% (v/v) glycerol, 40 mM MgCl$_2$, 50 μl of cellular extract, 100 μM acetoacetyl-CoA and 150 mM potassium acetate as carboxylic acid source. One unit of enzyme activity is defined as the amount of enzyme required to convert 1 μmol of acetoacetyl-CoA to product in 1 min under these conditions ($\epsilon$=8.0 mM$^{-1}$cm$^{-1}$).

3-Oxoacid-CoA-Transferase Activity Assay

Activity was measured by monitoring the increase in A310 corresponding to the formation of acetoacetyl-CoA, as previously described (Howard et al., 1986). The assay contained 67 mM acetoacetate (Aldrich), 300 μM succinyl-CoA and 15 mM MgCl$_2$ in 50 mM Tris-HCl pH 9.1. Under the experiment conditions, $\epsilon$=7,800 M$^{-1}$cm$^{-1}$.

Results

Figure 7A:
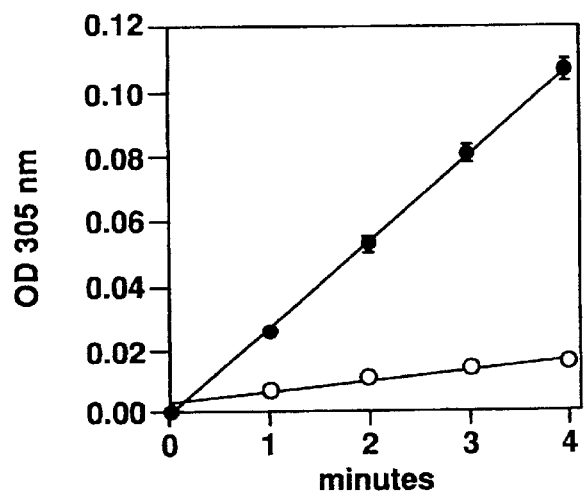
FIGS. 7A, 7B and 7C show the results of different CoA-t activity assays. Cellular lysates (CL) of *E. coli* JM105 transfected with pUreA (open circles) or pCoA-t (closed circles) were prepared and CoA-t activities measured on different substrates using spectrophotometric assays. (FIG.
Figure 7B:
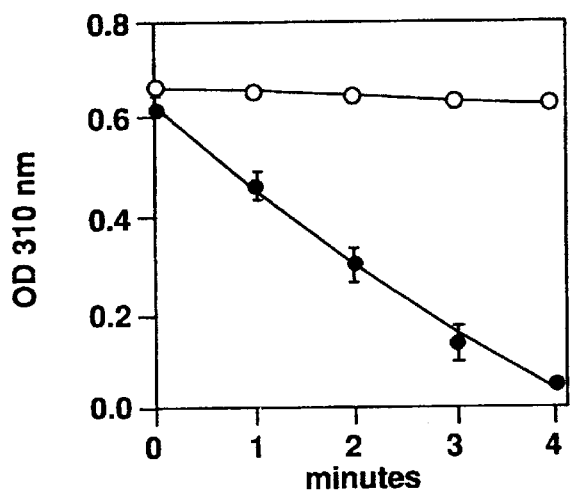
Figure 7C:
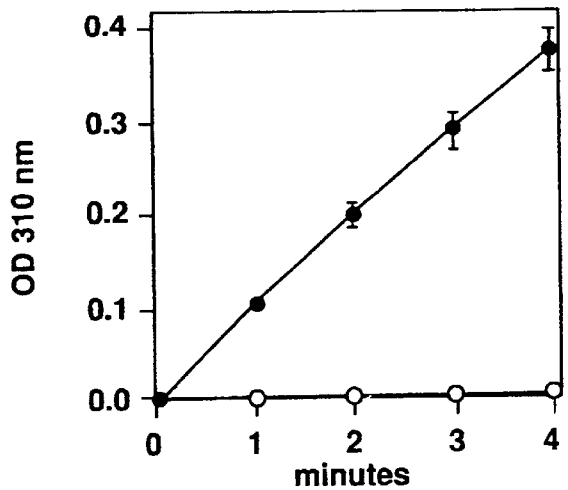

The enzymatic activity base line was determined using cellular extracts of E. coli transfected with pUreA (pKK223-3 containing 719 base pairs of Hp ureaseA gene). All three enzymatic activities tested were clearly detected over basal levels FIGS. 7A, 7B and 7C. E. coli crude extracts expressing pCoA-t showed a 10-, 22- and 11,000-fold increase in 3-oxoadipate CoA, butyrate-acetoacetate CoA and 3-oxoacid CoA-transferase activities, respectively, compared to cells expressing pUreA (FIG. 7A, 7B and 7B).

TABLE 5

CoA-transferase activities reconstituted in E. coli JM 105 cells transfected with recombinant plasmids.

| | Specific activity (mU/mg ± SD) | | |
|---|---|---|---|
| Plasmid | 3-oxoadipate coA-T EC 2.8.3.6 | Acetoacetate coA-T EC 2.8.3.9 | 3-oxoacid coA-T EC 2.8.3.5 |
| a) pUreA | 0.10 ± 0.02 | 2.13 ± 0.06 | 0.25 ± 0.06 |
| b) pCoA-t | 1.0 ± 0.1 | 44 ± 4 | 2800 ± 200 |
| fold increase b)/a) | 10x | 22x | 11,000x |

CoA-t activities were measured with the following substrates: succinyl CoA and β-ketoadipate for EC 2.8.3.6, acetocetyl-CoA and acetate for EC 2.8.3.9 and succinyl-CoA and acetoacetate for EC 2.8.3.5 as CoA donors and acceptors, respectively. Specific activites were calculated in function of the protein concentration of total cellular extracts as described herein.

Example 9

Inability of Hp CoA-transferase Negative Mutants to Colonize Mouse Stomach

To determine the importance of this enzyme for Hp survival, Hp CoA-t Subunit A negative and CoA-t Subunit B negative mutants were constructed using a well established protocol (Haas et al., MolMicrobiol, 1993; Kahrs et al., Gene 1995) The procedure involves inactivation of the cloned CoA-t Subunit A or CoA-t Subunit B genes by insertion of the TnMax5 mini-transposon and reintroduction of the mutated genes into H. pylori by natural transformation to allow allelic replacement of the intact chromosomal genes by the mutated genes Several independent transposon insertions in the target plasmid pDB6, containing the target gene, were obtained. Two of them, designated pDB6-5 and pDB6-2, contained TnMax5 at positions 424 and 883, respectively and were selected for shuttle mutagenesis of a mouse-adapted H. pylori strain P49 (Kleanthous et al, 1996) The resulting mutants obtained from pDB6-5 and pDB6-2 were designated CoATA⁻ and CoATB⁻, respectively.

To confirm that the CoA-t Subunit A and CoA-t Subunit B genes are disrupted by TnMAx5 in the CoA transferase negative mutants, chromosomal DNA was prepared from the parental strain and the transformants and the genes encoding the A and the B subunit of Helicobacter CoA transferase were amplified by polymerase chain reaction (PCR). PCR amplification of the CoA-t Subunit A gene yielded the expected DNA fragment of 724 bp for the parental strain and the CoATB⁻ mutant and a DNA fragment of 1800 bp for the CoATA⁻ mutant corresponding to the combined size of CoA-t Subunit A gene plus TnMax5 (1.100 bp). Similarly, amplification of the CoA-t Subunit B gene gave a fragment of the expected size (648 bp) for the parental strain and the CoATA⁻ mutant, whereas a 1,800 bp band, equivalent to the sum of CoA-t Subunit B gene and the transposable element sizes, was obtained from CoATB⁻ mutant.

To analyze the effect of chromosomal DNA sequence replacement on protein synthesis, whole-cell lysates (CL) from Hp P49 and CoATA⁻ and CoATB⁻ mutants were analyzed by immunoblotting using anti-A and anti-B subunits antibodies. The A subunit (apparent molecular mass of 26,000) and the B subunit ($M_r$ 24,000) were detected by the corresponding antibodies in the CL of Hp 69A, Hp P49 and in an E. coli lysate producing the recombinant Helicobacter CoA transferase. In contrast, no protein corresponding to the A nor to the B subunit was observed in the lysates obtained from either mutant.

To further evaluate the functional consequence of allelic replacement of CoA-t Subunit A and Subunit B genes, succinyl CoA: acetoacetate CoA transferase activity was measured as formation of acetoacetyl CoA in function of time in the presence of iodoacetamide to inhibit endogenous thiolase activity. While Hp P49 showed a linear accumulation of product, CoATA⁻ and CoATB⁻ mutant activities were hardly distinguishable from the base line. Thus, CoATA⁻ and CoATB⁻ mutants do not harbor succinyl CoA: acetoacetate CoA transferase activity.

To determine the importance of the succinyl CoA: acetoacetate CoA transferase in vivo, BALB/c germ free mice were infected 2–3 times with Hp strain P49 and the CoATA⁻ and CoATB⁻ mutants. Ten to twelve days after the last infection, mice were sacrificed and the presence of bacteria evaluated in half stomach by an enzymatic test based on urease activity (Corthésy et al, 1995) or by PCR. When mice were infected with the H. pylori mouse adapted strain, 75% (9/12) of them became infected after two doses of 5×10⁸ bacteria given intragastically (exp 1) and 100% (12/12) after three doses (exp 2). In each experiment, mice were infected concomittantly under the same conditions with the isogenic CoATA⁻ and CoATB⁻ mutants. The inoculum size of the parental strain and the mutants was confirmed to be identical after serial dilution plating and estimation of the colony forming units. In both experiments, mice infected with CoATA⁻ and CoATB⁻ mutants were found to be free of bacteria, as assessed by measuring urease activity at the moment of sacrifice. In order to rule out a detection problem, urease activity of the parental strain and the mutants was analyzed and found to be identical. The stability of the mutants of each inoculum was evaluated by PCR amplification of CoA-t Subunit A and Subunit B genes from purified bacterial DNA. To confirm the results obtained using the urease test, total DNA was isolated from half stomach of animals and CoA-t Subunit A and Subunit B genes amplified by PCR. H. pylori was detected only in the stomach of mice infected with the parental strain, which is in complete agreement with the measurements of urease activity. Therefore, CoATA⁻ and CoATB⁻ mutants are unable to colonize BALB/c mice, suggesting that CoA-transferase is essential for H. pylori survival in a host organism.

Example 10

Measurement of 3-oxoacid CoA-transferase Activity in H. Pylori

The activity assay was performed as described in Example 8, using H. pylori cell lysates.

Results

The only CoA-transferase activity detected in H. pylori lysates was the one leading to the formation of acetoacetyl CoA from succinyl CoA and acetoacetate in the presence of $Mg^{2+}$. The rate of formation of acetoacetyl CoA in H. pylori lysates was lower than the one measured in transformed E. coli and was not linear over time, indicating that acetoacetyl CoA was processed concomitantly. The addition of 2 mM iodoacetamide, an inhibitor of acetoacetyl CoA thiolase resulted in a 2.5-fold increase of CoA transferase specific activity (60±2 mU/mg vs 25±2 mU/mg without iodoacetamide) and in a linear accumulation of acetoacetyl CoA.

Example 11

Effect of Inhibitors on Hp 3-oxoacid CoA-transferase Activity

The activity assay was performed as described in Example 8 in the presence of the indicated inhibitors. The results are presented below in Table 6

TABLE 6

Effect of inhibitors on 3-oxoacid CoA transferase activity reconstituted in E. coli or endogenous in H. pylori

| substances (50 nM) | Specific activity (mU/mg ± SD) | |
| --- | --- | --- |
|  | E. coli transformed with pCOA-t | H pytori |
| none | 2255 ± 7 | 25 ± 1 |
| monosodium aspartate | 1859 ± 151 | 24 ± 1 |
| disodium malonate | 1823 ± 162 | 27 ± 4 |
| monosodium malate | 131 ± 0 | 22 ± 8 |
| methyl succinic acid | 67 ± 51 | 0 ± 1 |
| methyl succinic ester | 58 ± 49 | 14 ± 3 |
| glutaric acid | 31 ± 7 | 16 ± 5 |
| mercapto succinic acid | 16 ± 13 | 2 ± 2 |

Example 12

Measurement of Reverse Reaction of CoA-transferase

As described above, CoA-transferase also catalyzes the reverse reaction, acetoacetyl CoA+succinate→acetoacetate+succinyl CoA. This additional 3-oxoacid CoA-transferase activity is examined in transformed E. coli and H. pylori by measuring the disappearance of acetoacetyl CoA at 310 nm. The results are presented below in Table 7.

TABLE 7

3 oxo acid CoA-transferase activity in transformed *E. coli* and *H. pylori* as measured by disappearance of accloacetyl CoA at 310 nm (reverse reaction: acetoacetyl CoA + succinate- > acetoacetate + succinyl CoA)

|  | Specific activity (mU/mg) |
| --- | --- |
| *E. coli* + pCOAT | 37846 |
| *E. coli* + pUreA | 83 |
| Hp 69A | 227 ± 4 |
| Hp 69A + 2 mM iodoacetamide | 257 ± 0 |

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated and purified polypeptide comprising an amino acid sequence of a CoA transferase or thiolase enzyme or an immunogenic fragment at least 50 consecutive amino acids in length of said enzyme, wherein said enzyme is derived from a Helicobacter bacterium that can propagate in a human stomach.

2. The isolated polypeptide of claim 1, wherein said enzyme is a CoA-transferase.

3. The isolated polypeptide of claim 1, wherein said amino acid sequence comprises the entire amino acid sequence of SEQ ID NO.:02.

4. The isolated polypeptide of claim 1, wherein said amino acid sequence comprises the entire amino acid sequence of SEQ ID NO.:03.

5. The isolated polypeptide of claim 1, wherein said enzyme is a thiolase.

6. The isolated polypeptide of claim 1, wherein said bacterium is a *Helicobacter pylori* bacterium.

7. The isolated polypeptide of claim 1, wherein said amino acid sequence comprises the entire amino acid sequence of SEQ ID NO:17.

8. An isolated polypeptide comprising the amino acid sequence of SEQ ID NO:02.

9. An isolated polypeptide comprising the amino acid sequence of SEQ ID NO:03.

10. An isolated polypeptide comprising the amino acid sequence of SEQ ID NO:17.

11. the isolated polypeptide of claim 2, wherein said CoA-transferase comprises the amino acid sequence of SEQ ID NO:02 or SEQ ID NO:03 or both.

12. The isolated polypeptide of claim 5, wherein said thiolase comprises the amino acid sequence of SEQ ID NO:17.

\* \* \* \* \*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 1395 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
CGGGCGCGTC GTTGTGCGTG GGCGGCGGTC AAGGGCTATC AGTGGTAGTT GAACAAAAAT      60

AAGGAGAATG AGATGAACAA GGTTATAACC GATTTAGACA AAGCATTGAG CACATTAAAA     120

GACGGGGACA CTATTTTAGT GGGCGGTTTT GGGCTGTGCG GGATACCCGA ATACGCCATT     180

GATTACATTT ATAAGAAAGG CATTAAGGAT TTGATTGTCG TGAGCAATAA TTGTGGCGTT     240

GATGATTTTG GGCTTGGCAT TCTTTTAGAA AAAAAGCAGA TCAAAAAGAT TATCGCTTCG     300

TATGTGGGAG AAAATAAGAT TTTTGAATCG CAAATGCTGA ACGGAGAAAT TGAAGTCGTT     360

TTGACACCGC AAGGCACCCT GGCTGAAAAC TTGCGCCCTG GAGGGGCTGG GATACCGCTT     420

ACTACACCCC AACCAGGGGT TGGGACTTTA ATCGCTCCAA GGCAAGGAAT CCAAGGGAGT     480

TTAACGGCAA GGGAGTATAT TTTAGAAAGA GCCATAACAG GCGATTATGG GCTTATCAAA     540

GCTTATAAAA GCGACACTCT TGGGAATTTG GTGTTTAGAA AAACAGCTAG AAATTTCAAT     600

CCCTTGTGCG CGATGGCAGC AAAAATATGC GTTGCTGAAG TGGAAGAAAT TGTCCCGGCC     660

GGGGAATTAG ACCCAGATGA AATACACTTG CCAGGAATCT ATGTGCAACA CATCTATAAG     720

GGCGAGAAAT TTGAAAAACG GATAGAAAAA ATCACGACAA GGAGCGCGAA ATGAGAGAGG     780

CTATCATTAA AAGAGCGGCA AAGGAACTAA AAGAGGGCAT GTATGTGAAT TTAGGGATAG     840

GCTTGCCCAC GCTGGTGGCT AATGAAGTGA GCGGGATGAA TATCGTTTTC CAGAGCGAGA     900

ACGGGTTATT AGGGATTGGC GCTTACCCTT TAGAGGGGAG CGTTGATGCG GATCTCATCA     960

ACGCAGGAAA GGAAACCGTA ACCGTGGTGC CGGGCGCTTC GTTTTTCAAT AGCGCGGATT    1020

CGTTTGCGAT GATTCGTGGG GGGCATATTG ATTTAGCGAT TTTAGGAGGG ATGGAAGTCT    1080
```

-continued

```
CACAAAATGG GGATTTGGCT AATTGGATGA TCCCTAAAAA GCTCATAAAA GGCATGGGAG    1140

GGGCTATGGA TCTGGTGCAT GGCGCTAAAA AAGTGATTGT CATCATGGAG CATTGCAACA    1200

AATACGGGGA GTCTAAAGTG AAAAAGGAAT GCTCATTGCC CTTAACAGGA AAAGGCGTGG    1260

TGCATCAATT GATAACGGAT TTAGCGGTGT TTGAATTTTC CAATAACGCC ATGAAATTAG    1320

TGGAATTGCA AGAGGGGGTC AGCCTTGATC AAGTGAGAGA AAAACAGAA GCCGAATTTG     1380

AAGTGCACCT ATAGC                                                    1395
```

(2) INFORMATION FOR SEQ ID NO:2:

(i) SEQUENCE CHARACTERISTICS:
       (A) LENGTH: 241 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

```
Leu Asn Lys Asn Lys Glu Asn Glu Met Asn Lys Val Ile Thr Asp Leu
 1               5                  10                  15

Asp Lys Ala Leu Ser Thr Leu Lys Asp Gly Asp Thr Ile Leu Val Gly
                20                  25                  30

Gly Phe Gly Leu Cys Gly Ile Pro Glu Tyr Ala Ile Asp Tyr Ile Tyr
            35                  40                  45

Lys Lys Gly Ile Lys Asp Leu Ile Val Val Ser Asn Asn Cys Gly Val
        50                  55                  60

Asp Asp Phe Gly Leu Gly Ile Leu Leu Glu Lys Gln Ile Lys Lys
65                  70                  75                  80

Ile Ile Ala Ser Tyr Val Gly Glu Asn Lys Ile Phe Glu Ser Gln Met
                85                  90                  95

Leu Asn Gly Glu Ile Glu Val Val Leu Thr Pro Gln Gly Thr Leu Ala
                100                 105                 110

Glu Asn Leu Arg Pro Gly Gly Ala Gly Ile Pro Leu Thr Thr Pro Gln
            115                 120                 125

Pro Gly Val Gly Thr Leu Ile Ala Pro Arg Gln Gly Ile Gln Gly Ser
        130                 135                 140

Leu Thr Ala Arg Glu Tyr Ile Leu Glu Arg Ala Ile Thr Gly Asp Tyr
145                 150                 155                 160

Gly Leu Ile Lys Ala Tyr Lys Ser Asp Thr Leu Gly Asn Leu Val Phe
                165                 170                 175

Arg Lys Thr Ala Arg Asn Phe Asn Pro Leu Cys Ala Met Ala Ala Lys
                180                 185                 190

Ile Cys Val Ala Glu Val Glu Glu Ile Val Pro Ala Gly Glu Leu Asp
            195                 200                 205

Pro Asp Glu Ile His Leu Pro Gly Ile Tyr Val Gln His Ile Tyr Lys
        210                 215                 220

Gly Glu Lys Phe Glu Lys Arg Ile Glu Lys Ile Thr Thr Arg Ser Ala
225                 230                 235                 240

Lys
```

(2) INFORMATION FOR SEQ ID NO:3:

(i) SEQUENCE CHARACTERISTICS:
       (A) LENGTH: 219 amino acids
       (B) TYPE: amino acid (C) STRANDEDNESS: single
            (D) TOPOLOGY: linear (ii) MOLECULE TYPE: peptide (xi) SEQUENCE DESCRIPTION: SEQ ID NO:3:

Lys Thr Asp Arg Lys Asn His Asp Lys Glu Arg Glu Met Arg Glu Ala
1               5                   10                  15

Ile Ile Lys Arg Ala Ala Lys Glu Leu Lys Glu Gly Met Tyr Val Asn
            20                  25                  30

Leu Gly Ile Gly Leu Pro Thr Leu Val Ala Asn Glu Val Ser Gly Met
        35                  40                  45

Asn Ile Val Phe Gln Ser Glu Asn Gly Leu Leu Gly Ile Gly Ala Tyr
    50                  55                  60

Pro Leu Glu Gly Ser Val Asp Ala Asp Leu Ile Asn Ala Gly Lys Glu
65                  70                  75                  80

Thr Val Thr Val Val Pro Gly Ala Ser Phe Phe Asn Ser Ala Asp Ser
                85                  90                  95

Phe Ala Met Ile Arg Gly Gly His Ile Asp Leu Ala Ile Leu Gly Gly
            100                 105                 110

Met Glu Val Ser Gln Asn Gly Asp Leu Ala Asn Trp Met Ile Pro Lys
        115                 120                 125

Lys Leu Ile Lys Gly Met Gly Gly Ala Met Asp Leu Val His Gly Ala
    130                 135                 140

Lys Lys Val Ile Val Ile Met Glu His Cys Asn Lys Tyr Gly Glu Ser
145                 150                 155                 160

Lys Val Lys Lys Glu Cys Ser Leu Pro Leu Thr Gly Lys Gly Val Val
                165                 170                 175

His Gln Leu Ile Thr Asp Leu Ala Val Phe Glu Phe Ser Asn Asn Ala
            180                 185                 190

Met Lys Leu Val Glu Leu Gln Glu Gly Val Ser Leu Asp Gln Val Arg
        195                 200                 205

Glu Lys Thr Glu Ala Glu Phe Glu Val His Leu
    210                 215

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:4:

GATAAACCGG CACC                                                         14

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:5:

GCGGGCGCGT CGTT                                                         14

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:6:

GGAATTCATG AACAAGGTTA TAACCG                                      26

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:7:

GGAATTCTGC AGCTATAGGT GCACTTCAAA TTCG                             34

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:8:

GCTCTAGAGC CTCTCATTTC GCGCTCCTTG TCG                              33

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:9:

CCATCGATAT CACGACAAGG AGCGCGAAAT GA                                32

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:10:

CGGGATCCCG ATGAACAAGG TTATAACCG                                   29

(2) INFORMATION FOR SEQ ID NO:11:

(i) SEQUENCE CHARACTERISTICS:

```
            (A) LENGTH: 36 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:11:

GGAATTCGTC GACGCTATAG GTGCACTTCA AATTCG                            36

(2) INFORMATION FOR SEQ ID NO:12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:12:

GCTCTAGAGC GATAAAACCG GCACC                                        25

(2) INFORMATION FOR SEQ ID NO:13:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:13:

CCATCGATGG GCGGGCGCGT CGTT                                         24

(2) INFORMATION FOR SEQ ID NO:14:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:14:

GGAATTCGTC GACTCTCATT TCGCGCTCCT TGTCG                             35

(2) INFORMATION FOR SEQ ID NO:15:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:15:

CGGGATCCCG ATGAGAGAGG CTATCATTAA AAG                               33

(2) INFORMATION FOR SEQ ID NO:16:

(i) SEQUENCE CHARACTERISTICS:
            (A) LENGTH: 301 base pairs
            (B) TYPE: nucleic acid
            (C) STRANDEDNESS: double
            (D) TOPOLOGY: linear
```

-continued (ii) MOLECULE TYPE: DNA (genomic)

(xi) SEQUENCE DESCRIPTION: SEQ ID NO:16:

| | | | | | |
|---|---|---|---|---|---|
| GAATTCATCA | GGGATCAATG | ATGGCGCGAG | CATTATCATT | TTATGCAGCG | CTAAAAAAGC | 60 |
| GCAAAAATTA | GGGTTAAAAG | CCATGGCTAC | TATCAGGGGG | TTTGGTTTGG | GTGGTTGCAG | 120 |
| TCCGGATATA | ATGGGTATAT | GCCCTAGTAT | TGCGATTAAA | AACAATCTTA | AAAATGTCAA | 180 |
| AATGAATCTC | AATGACATCA | ATCTTTTTGA | ACTCAATGAA | GCCTTTGCCG | CGCAAAGTCT | 240 |
| AGCCGTGTTA | AAAGAGCTTG | AATTAAACCC | CAATATAGTG | AATGTGAATG | GAGGCGCGAT | 300 |
| A | | | | | | 301 |

(2) INFORMATION FOR SEQ ID NO:17:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Asn Ser Ser Gly Ile Asn Asp Gly Ala Ser Ile Ile Ile Leu Cys
 1               5                  10                  15

Ser Ala Lys Lys Ala Gln Lys Leu Gly Leu Lys Ala Met Ala Thr
                20                  25                  30

Ile Arg Gly Phe Gly Leu Gly Gly Cys Ser Pro Asp Ile Met Gly
                35                  40                  45

Ile Cys Pro Ser Ile Ala Ile Lys Asn Asn Leu Lys Asn Val Lys
                50                  55                  60

Met Asn Leu Asn Asp Ile Asn Leu Phe Glu Leu Asn Glu Ala Phe
                65                  70                  75

Ala Ala Gln Ser Leu Ala Val Leu Lys Glu Leu Glu Leu Asn Pro
                80                  85                  90

Asn Ile Val Asn Val Asn Gly Gly Ala Ile
                95                  100
```